United States Patent [19]

Minami et al.

[11] 4,103,011
[45] Jul. 25, 1978

[54] NOVEL PENICILLIN COMPOUNDS AND PROCESS FOR PREPARATION THEREOF

[75] Inventors: Shinsaku Minami, Yamatokouriyama; Yoshiyuki Takase, Amagasaki, both of Japan

[73] Assignee: Dainippon Pharmaceutical Co., Ltd., Osaka, Japan

[21] Appl. No.: 811,445

[22] Filed: Jun. 29, 1977

[30] Foreign Application Priority Data

Jun. 30, 1976 [JP] Japan .................................. 51-78085
Aug. 12, 1976 [JP] Japan .................................. 51-96713

[51] Int. Cl.² ..................... A61K 31/43; C07D 499/68
[52] U.S. Cl. ................................... 424/251; 128/272; 424/271; 260/239.1
[58] Field of Search ............... 260/239.1; 424/271, 424/251

[56] References Cited

U.S. PATENT DOCUMENTS

| | | | |
|---|---|---|---|
| 3,433,784 | 3/1969 | Long et al. | 260/239.1 |
| 3,887,557 | 6/1975 | Minami et al. | 260/239.1 |
| 3,939,150 | 2/1976 | Murakami et al. | 260/239.1 |
| 3,953,428 | 4/1976 | Murakami et al. | 260/239.1 |
| 3,954,734 | 5/1976 | Doub et al. | 260/239.1 |
| 3,992,371 | 11/1976 | Tobiki et al. | 260/239.1 |
| 4,003,887 | 1/1977 | Tobiki et al. | 260/239.1 |

*Primary Examiner*—Gerald A. Schwartz
*Attorney, Agent, or Firm*—Wenderoth, Lind & Ponack

[57] ABSTRACT

A penicillin compound of the formula

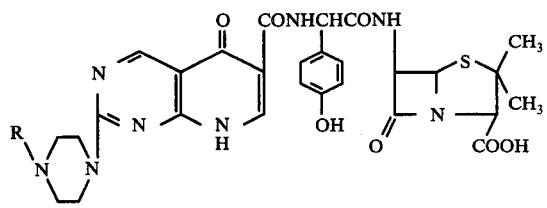

wherein R is a formyl or acetyl group, and a nontoxic pharmaceutically acceptable salt thereof. The penicillin compound is prepared by (A) reacting a compound of the formula

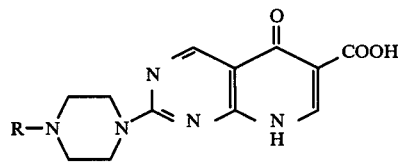

or its salt or its reactive derivative at the carboxyl group, with 6-α-amino-p-hydroxybenzylpenicillin or its salt or its derivative, or reacting a compound of the formula

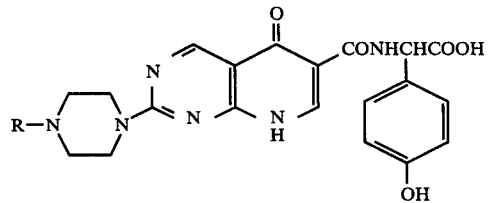

or its salt or its reactive derivative at the carboxyl group, with 6-aminopenicillanic acid or its salt or its derivative, (B) optionally hydrolyzing or catalytically hydrogenolyzing the reaction product, and (C) optionally converting the reaction product to a nontoxic pharmaceutically acceptable salt. The penicillin compound has low toxicity and superior antibacterial activity especially against bacteria of the genus Pseudomonas and is suitable for parenteral administration, especially for an intramuscular, intravenous or subcutaneous injection.

13 Claims, No Drawings

NOVEL PENICILLIN COMPOUNDS AND PROCESS FOR PREPARATION THEREOF

This invention relates to novel penicillin compounds having superior antibacterial activity, injections containing the novel penicillin compounds, preparations for forming injections, and to a process for preparing the penicillin compounds.

The novel penicillin compounds of the invention are compounds of the following formula

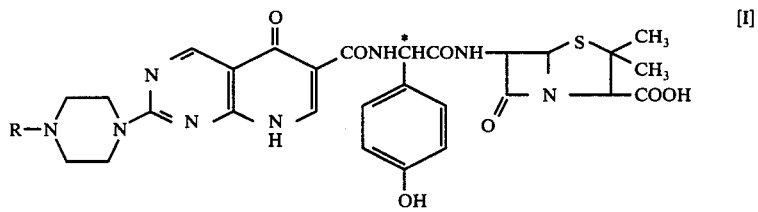

[I]

wherein R is a formyl or acetyl group, and their nontoxic pharmaceutically acceptable salts.

The nontoxic pharmaceutically acceptable salts are salts formed between the penicillin compounds of formula (I) and nontoxic pharmaceutically acceptable inorganic or organic bases, and include, for example, nontoxic metal salts of the penicillin compounds such as alkali metal salts (e.g., sodium or potassium salts) and alkaline earth metal salts (e.g., calcium or magnesium salts). Preferred nontoxic salts are sodium and potassium salts, the former being particularly preferred.

The penicillin compounds of formula [I] exist in two tautomers (keto-type and enol-type) of formulae [I] and [I'] shown below. In the present application, these tautomers are inclusively expressed by the keto-type of formula [I] below.

formula [I], on the basis of the steric configuration concerning this carbon, include a D-isomer, an L-isomer, and a mixture of these isomers (to be referred to as D,L mixture). All of these isomers and mixtures are expressed by formula [I] given hereinabove.

Sometimes, the penicillin compounds of formula [I] exist in the form of hydrates, and such hydrates are also included within the penicillin compounds of the invention expresses by formula [I].

It is an object of this invention to provide novel penicillin compounds having superior antibacterial activity against Gram-negative bacteria as well as against Gram-positive bacteria, and a process for their preparation.

Another object of this invention is to provide novel penicillin compounds having superior anitbacterial activity against the genus Pseudomonas including Pseudomonas aeruginosa, Ampicillin-resistant bacteria and injectable compositions containing these compounds.

Still another object of this invention is to provide injections for intramuscular, intravenous or subcutaneous administration and preparations for forming such injections, which contain a novel and selected penicillin compound having superior antibacterial activity against the various bacteria mentioned and having very low toxicity to warm-blooded animals including humans.

Other objects and advantages of the invention will become apparent from the following description.

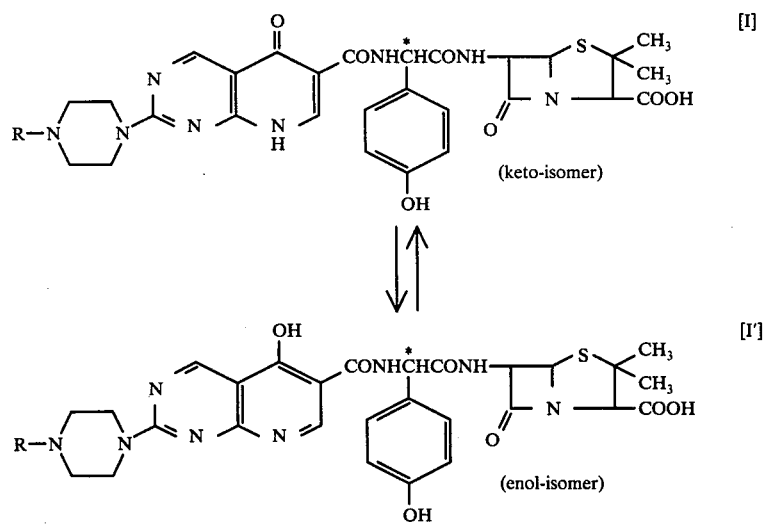

Since the asterisked carbon atom ascribable to the α-carbon of p-hydroxyphenylglycine residue in formulae [I] and [I'] is an asymmetric carbon, the penicillin compouns of the invention expressed by compounds The novel penicillin compounds of the invention are inclusively expressed by formula [I], but are individually expressed by the following formulae [Ia] and [Ib].

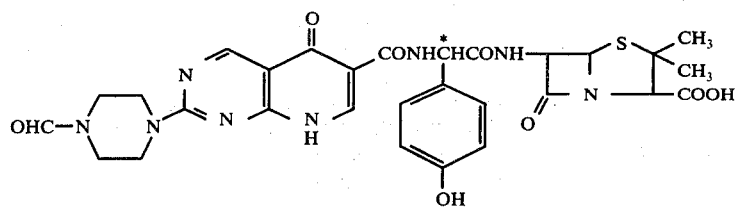

Formula [Ia]

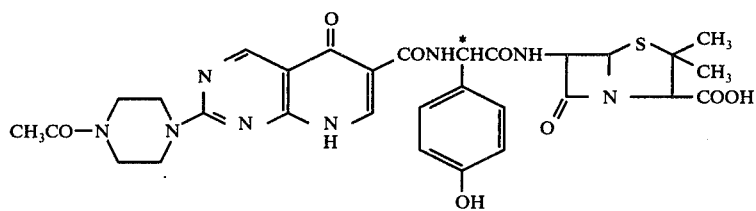

Formula [Ib]

The asterisked carbon atom in each of formulae [Ia] and [Ib] is an asymmetric carbon atom, and on the basis of its steric configuration, each incudes a D-isomer, L-isomer, and a D,L-mixture. For the sake of convenience, the penicillin compound of formula [Ia] will be sometimes referred to as "formylpiperazine derivatives", and the penicillin compounds of formula [Ib], "acetylpiperazine derivatives".

D-isomers show especially superior antibacterial activity and low toxicity among the formyl- and acetyl-piperazine derivatives, and are named as follows:

D-formylpiperazine derivative
D-α-[5,8-dihydro-2-(4-formyl-1-piperazinyl)-5-oxopyrido[2,3-d]pyrimidine-6-carboxamido]-p-hydroxybenzyl-penicillin D-acetylpiperazine derivative
D-α-[5,8-dihydro-2-(4-acetyl-1-piperazinyl)-5-oxopyrido[2,3-d]pyrimidine-6-carboxamido]-p-hydroxybenzyl-penicillin Ampicillin derivatives of the following formula

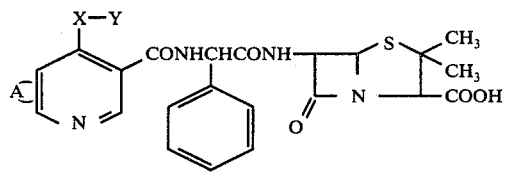
(X)

wherein A is a fused aromatic carbocyclic ring or six-membered heteroaromatic ring containing nitrogen as a heteroatom, X is a sulfur atom or an oxygen atom and Y is a hydrogen atom, an alkanolyl group with 1 to 8 carbon atoms or an alkoxycarbonyl group with 2 to 5 carbon atoms, which result from the substitution of α-amino group of Ampicillin with an acyl group containing a heterocyclic ring have heretofore been known (British Pat. No. 1,387,251). The British Patent discloses only the acylation of Ampicillin, and does not at all disclose the acylation of Ampicillin with a specific 5,8-dihydro-5-oxopyrido[2,3-d]pyrimidinecarboxylic acid residue (to be referred to as pyridopyrimidinecarboxylic acid residue) of the following formula [Ic] in which the 2-position is substituted by a 4-formyl-1-piperazinyl- or 4-acetyl-1-piperazinyl group as in the present invention.

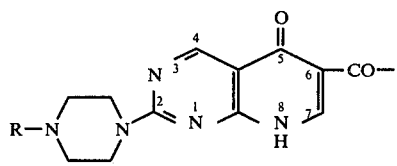
[Ic]

wherein R is a formyl or acetyl group.

As will be shown hereinbelow in Tables I to III, the investigations of the present inventors show that the novel penicillin compounds of the present invention having a moiety of Amoxicillin or its isomer expressed by formula [I] ([Ia] and [Ib]) have far supeior antibacterial activity, especially against Pseudomonas aeruginosa, than penicillin derivatives resulting from the substitution of the α-amino group of Ampicillin by a specific pyridopyrimidinecarboxylic acid residue of formula [Ic] of the present invention.

On the other hand, U.S. Pat. No. 4,003,887 and the corresponding British Pat. No. 1,446,484 disclose N-acylated Amoxicillin derivatives of the following formula

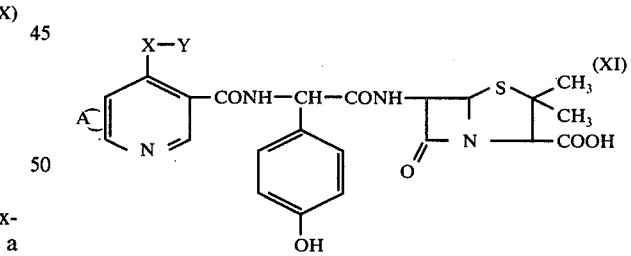
(XI)

wherein ring A is a benzene ring or 5- or 6-membered heteroaromatic ring containing one or two nitrogen atoms as heteroatoms, on which one or more of lower alkyl, lower alkoxy, lower alkylthio, lower haloalkyl, lower alkylenedioxy, halogen, hydroxyl, nitro, free or protected amino, lower alkylamino, di(lower)alkylamino, and lower alkanoylamino may be present; X is oxygen or sulfur and Y is hydrogen, lower alkoxycarbonyl or lower alkanoyl.

The specification of Japanese Laid-Open Patent Publication No. 82,683/74 corresponding to U.S. Pat. No. 4,003,887 states very indefinitely that ring A in formula (XI) may have a substituent. The compounds specifically disclosed in this publication are the same as those disclosed in U.S. Pat. No. 4,003,887 which are within the definition of formula (XI) given above.

The novel penicillin compounds of the invention expressed by formula [I] ([Ia] and [Ib]) do not fall within the definition of formula (XI) disclosed in U.S. Pat. No. 4,003,887 and the corresponding patents or patent applications filed in other countries.

U.S. Pat. No. 4,003,887 discloses an O-acyl derivative of a compound of the following formula

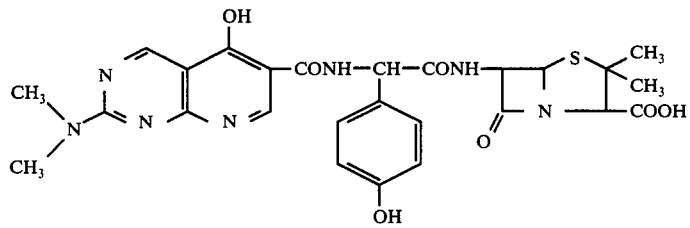

which results from the acylation of the hydroxyl group on the benzene nucleus of the Amoxicillin derivative (XIa) (to be referred to as 2-dimethylaminopyridopyrimidine derivative) wherein the amino group of Amoxicillin is acylated by a pyridopyrimidinecarboxylic acid residue substituted by a dimethylamino group in the 2-position. The compound (XIa) is structurally most similar to the novel penicillin compounds of this invention. However, as shown in Tables I to III, the novel penicillin compounds of this invention are characterized by their far superior antibacterial activity, especially against Pseudomonas aeruginosa, and far lower toxicity to warm-blooded animals than the compound (XI$_a$)

A compound of the following formula

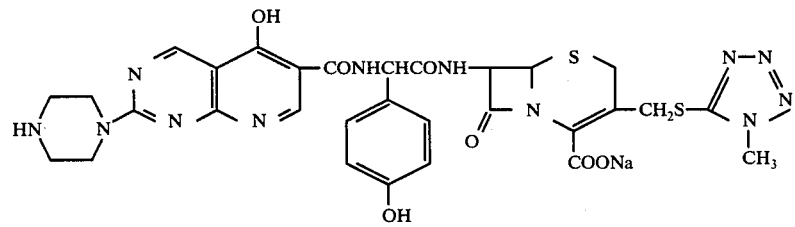

is also known (Belgian Pat. No. 833,063) although it is apparently of a different species.

This cephalosporin derivative has quite a different main skeleton from the penicillin compounds of the present invention, and the 2-position of the 5,8-dihydro-5-oxopyrido [2,3-d]pyrimidine moiety (to be referred to as pyridopyrimidine moiety) is substituted by a free 1-piperazinyl group, It is not substituted by a 4-formyl-1-piperazinyl group or a 4-acetyl-1-piperazinyl group as in the present invention.

The present inventors disclosed previously that compounds of the formula

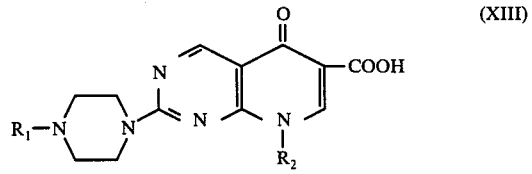

wherein $R_1$ is a moiety selected from one of the group consisting of hydrogen, alkyl having 1 to 4 carbon atoms, hydroxyalkyl having 2 to 4 carbon atoms, benzyl, benzyl substituted by methoxy, phenyl, propargyl or acyl selected from the group consisting of lower alkanoyl, trifluoroacetyl, lower alkoxycarbonyl and phenyl-substituted lower alkoxycarbonyl, and $R_2$ is a moiety selected from one of the group consisting of hydrogen, alkyl having 1 to 4 carbon atoms, alkyl having 2 to 4 carbon atoms substituted by hydroxy or halogen, vinyl, allyl or benzyl, have especially superior antibacterial activity against Gram-negative bacteria when $R_1$ is a hydrogen atom and $R_2$ is an ethyl group (Pipemidic acid) (U.S. Pat. No. 3,887,557). As shown in Tables I to III, this compound does not show any marked antibacterial activity against Gram-positive bacteria, whereas the novel penicillin compounds of this invention have superior antibacterial activity against Gram-positive bacteria as well as Gram-negative bacteria. It is further noted that the novel penicillin compounds of the invention differ structurally from the compound because the 2-position of the pyridopyrimidinecarboxylic acid residue as a structural factor is substituted specifically by a 4-formyl- or 4-acetyl-1-piperazinyl group, and the nitrogen atom at the 8-position is not substituted by a substituent such as an ethyl group. Compounds of formula (XIII) in which $R_2$ is a hydrogen atom do not substantially have an antibacterial activity, as shown in Table I.

As a result of screening the novel penicillin compounds of this invention and many compounds having similar structures, the present inventors found that because the 2-position of the pyridopyrimidine moiety is substituted by a 1-piperazinyl group containing two nitrogen atoms, the penicillin compounds of the invention expressed by formula [I] have markedly higher antibacterial activity, especially against Pseudomonas aeruginosa than penicillin compounds resulting from the substitution of the 2-position by a subsituted amino group containing one nitrogen atom, for example, dimethylamino, or a heterocyclic group containing one nitrogen atom for example a 1-pyrrolidinyl group; and that because the 4-position of the piperazinyl group is substituted by a formyl or acetyl group, the penicillin compounds of the invention have very low toxicity against warm-blooded animals while retaining high antibacterial activity in vivo.

The novel penicillin compounds of formula [I] and their nontoxic pharmaceutically acceptable salts can be produced, for example, by process (a) or process (b) described hereinbelow.

Process (a):

The outline of process (a) can be shown by the following reaction scheme.

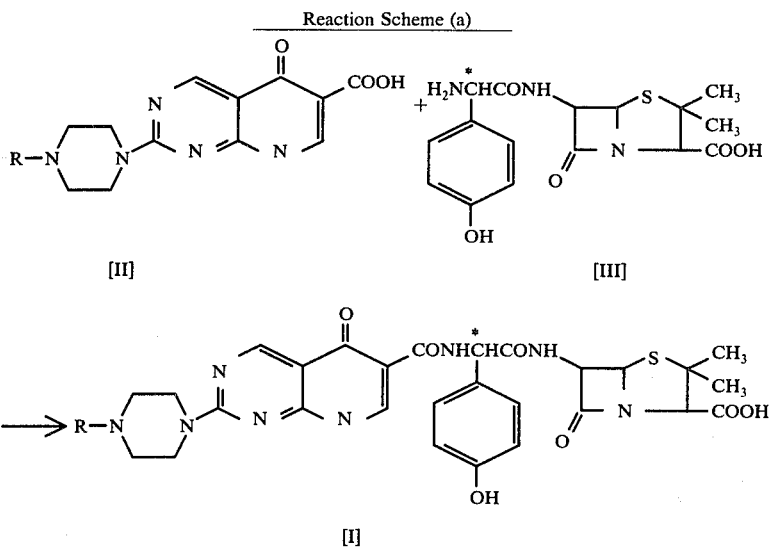

wherein R in formulae [I] and [II] is the same as defined above.

According to the process (a), the novel penicillin compound of this invention of formula [I] or its nontoxic pharmaceutically acceptable salt is prepared by reacting a 2-(4-formyl- or 4-acetyl-1-piperazinyl)-5,8-dihydro-5-oxopyrido[2,3-d]pyrimidine-6-carboxylic acid (generically referred to as "2-substituted pyridopyrimidinecarboxylic acid"; its 4-formyl substituted product is referred to as "2-FP substituted" instead of "2-substituted"; and its 4-acetyl substituted product is referred to as "2-AP substituted" instead of "2-substituted"), or its inorganic or organic salt, or its reactive derivative at the carboxyl group, with α-amino-p-hydroxybenzylpenicillin (to be abbreviated AHBP) or its inorganic or organic salt or a derivative convertible to AHBP in an aqueous or nonaqueous medium, then if desired hydrolyzing or catalytically hydrogenolyzing the resulting product to form a penicillin compound of this invention, and if further desired, converting the reaction product to a nontoxic pharmaceutically acceptable salt.

The reactive derivatives at the carboxyl group of the 2-substituted pyridopyrimidinecarboxylic acid of formaula [II] include all reactive derivatives known and used in the field of producing penicillins or cephalosporins. Specific examples are its acid anhydrides formed with acids such as alkylcarbonic acids (e.g., ethylcarbonic acid, isopropylcarbonic acid, iso- or sec-butylcarbonic acid), alkylcarboxylic acids (e.g., pivalic acid, pentanoic acid, iso-pentanoic acid, 2-ethylbutyric acid, and 2-ethylhexanoic acid), phosphoric acids (e.g., diethylphosphoric acid), and sulfonic acids (e.g., methanesulfonic acid); its reactive esters such as the p-nitrophenylester, trichlorophenyl ester, p-nitrophenylthio ester, N-hydroxypiperidine ester, N-hydroxysuccinimide ester or N-hydroxyphthalimide ester; its reactive amides such as N-carbonylimidazole or N-carbonyltetrazole; its acid halides such as acid chloride; and its acid azides.

The derivatives convertible to AHBP expressed by formula [III] are well known in the field of producing semi-synthetic penicillins, and can be used in process (a) of this invention. Typical examples of such derivatives are trimethylsilyl ester, trityl ester, p-nitrobenzyl ester, and phenacyl ester. Derivatives obtained by protecting the hydroxy group of the benzene nucleus of AHBP by, for example, an ethoxycarbonyl or benzyloxycarbonyl group can also be used.

The inorganic or organic salts of the 2-substituted pyridopyrimidinecarboxylic acid of formula [II] and/or AHBP of formula [III] include alkali metal salts such as sodium or potassium salts, and salts with organic bases such as triethylamine or N-ethylmorpholine.

The above reaction is carried out at $-40°$ to $40°$ C. for 1 to 10 hours in a solvent, preferably in the presence of a base. The solvent, base and other reaction conditions are substantially the same as those used in the chemistry of penicillins.

For example, when an anhydride derived from the 2-substituted pyridopyrimidinecarboxylic acid of formula [II] and ethyl chloroformate is used, the reaction is performed under cooling or at room temperature in the presence of a tertiary amine such as triethylamine or N,N-dimethylaniline in an inert solvent such as acetone, tetrahydrofuran, dimethylformamide, chloroform, dichloromethane or hexamethylphosphoramide, a mixture of such inert solvents, water, or a hydrous organic solvent.

When an N-hydroxysuccinimide ester of the 2-substituted pyridopyrimidinecarboxylic acid of formula [II] is used, the reaction is performed at 0° to 10° C. for 1 to 2 hours in the presence of a base such as triethylamine, lutidine, sodium hydroxide, or sodium carbonate in dimethylformamide, dichloromethane, dioxane, water or a mixture of these solvents.

The reaction of the 2-substituted pyridopyrimidinecarboxylic acid of formula [II] or its salt with AHBP of formula [III] or its salt is advantageously performed in the presence of a condensing agent such as N,N'-dicyclohexylcarbodiimide.

When the 2-substituted pyridopyrimidinecarboxylic acid or its salt or its reactive derivative of the carboxyl group is reacted with a derivative convertible to AHBP of formula [III], a reaction product having a moiety of AHBP convertible to the penicillin compound of this invention is sometimes formed according to reaction conditions. For example, it is when the carboxyl group of the reaction product is in the form of an ester such as a silyl ester, or when the hydroxyl group at the benzene nucleus of the reaction product is protected by a protective group such as an acyl group. In such a case, the product is further hydrolyzed or catalytically hydrogenolized in a customary manner known in the chemistry of penicillins to form the penicillin compound of this invention in a D,L-mixed form is obtained. As stated hereinabove, the novel penicillins of this invention in a D-form have especially high antibacterial activities.

Hence, in process (a), the type of the isomer of AHBP of formula [III] used as a starting material is selected according to the desired isomer of the final product.

Process (b):

The novel penicillin compounds of this invention can also be produced by process (b) mentioned below. The outline of process (b) can be expressed by the following reaction scheme (b).

Reaction scheme (b)

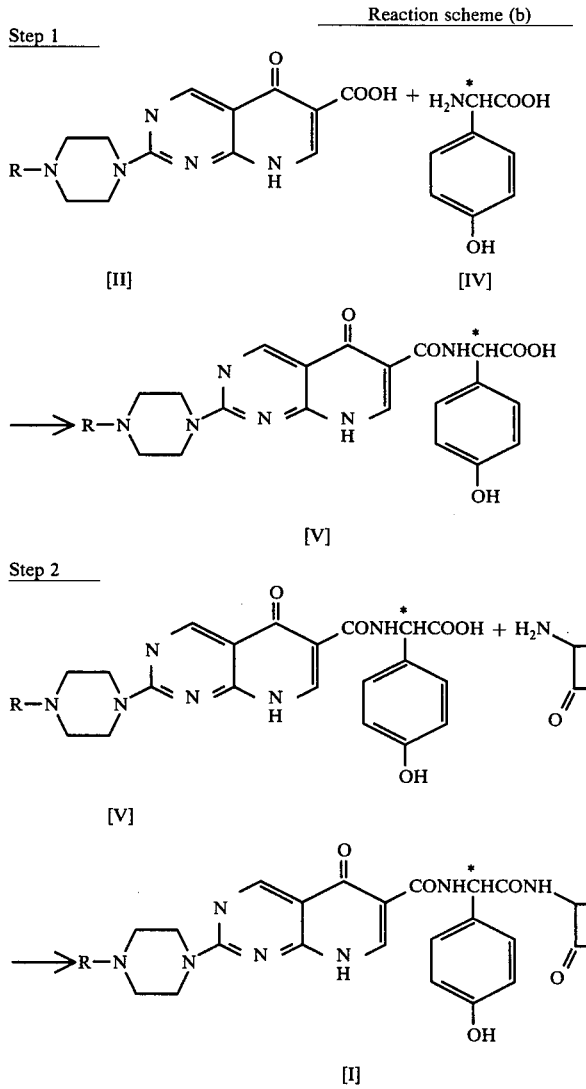

pound of this invention.

If desired, the penicillin compound of formula [I] so formed can be converted to its nontoxic pharmaceutically acceptable salt in a customary manner.

Since the asterisked carbon atom ascribable to the α-carbon of p-hydroxyphenylglycine residue in formula [III] in the reaction scheme (a) is an asymmetric carbon atom, AHBP of formula [III] includes an D-isomer, an L-isomer and a D,L-mixture.

If the D-isomer of AHBP is used as a starting material in process (a), the corresponding penicillin compound of this invention can be obtained in a D-form. If, the D,L-mixture of AHBP is used as a starting material, a wherein R is the same as defined above.

Process (b) schematically shown above consists of step 1 and step 2. Step 1 comprises reacting the 2-substituted pyridopyrimidinecarboxylic acid of formula [II], its inorganic or organic salt or its reactive derivative at the carboxyl group, with a p-hydroxyphenylglycine of formula [IV], or its inorganic or organic salt or its derivative to form α-[5,8-dihydro-2-(4-formyl or 4-acetyl-1-piperazinyl)-5-oxopyrido[2,3-d]pyrimidine-6-carboxamido]-p-hydroxyphenylacetic acid (to be referred to as 2-substituted pyridopyrimidinecarbonylglycine or PPCG). Step 2 comprises reacting PPCG, its salt or its reactive derivative at the carboxyl group with 6-aminopenicillanic acid of formula [VI] (to be referred to as 6-APA), its inorganic or organic salt or its derivative convertible to 6-APA, optionally hydrolyzing or catalytically hydrogenolyzing the resulting product to form a penicillin compound of formula [I], and optionally converting the reaction product to its nontoxic pharmaceutically acceptable salt.

The inorganic or organic salt or reactive derivative at the carboxyl group of the 2-substituted pyridopyrimidinecarboxylic acid of formula [II] used in step 1 may be the same as those described with regard to process (a).

The reaction of step 1 can be performed at −40° to +40° C., preferably at a temperature below room temperature, in the same aqueous or nonaqueous solvent as described above with regard to process (a).

PPCG of formula [V] formed by the reaction of step 1 is a novel compound.

In step 2, it is preferred to use PPCG in the form of its salt or its reactive derivative at the carboxyl group.

Such salts and reactive derivatives are the same as those described above with regard to the salts and reactive derivatives at the carboxyl group of 2-substituted pyridopyrimidinecarboxylic acid used in process (a). A derivative of PPCG in which the hydroxyl group at the benzene nucleus is protected by an acyl group may be used as a starting compound in step 2.

The salts of 6-APA or derivatives convertible to 6-APA used in step 2 may be substantially the same as the salts or derivatives of AHBP described above with regard to process (a) except for a derivative of AHBP in which the hydroxyl group at the benzene nucleus is protected. It is preferred to use 6-APA in the form of such a derivative in this reaction.

Preferred derivatives of 6-APA are, for example, its trimethylsilyl ester, trityl ester, p-nitrobenzyl ester, phenacyl ester, and O,N-bistrimethylsilyl derivative.

It is especially advantageous to react the derivative of 6-APA with the salt or reactive derivative at the carboxyl group of PPCG in an aprotic medium.

When 6-APA is used in the form of free carboxylic acid or its salt, the reaction of step 2 may also be performed in a protic medium or aqueous medium.

Preferably, the reaction of step 2 is carried out in a solvent at −40° to 40° C. for one hour to 2 days preferably in the presence of a base. The solvent, base and other reaction conditions are substantially the same as those used in the chemistry of penicillin.

For example, when an anhydride derived from PPCG of formula [V] and ethyl chloroformate is to be reacted with a derivative of 6-APA, the reaction is performed under cooling or at room temperature in the presence of a tertiary amine such as triethylamine or N,N-dimethylaniline in an inert solvent such as acetone, tetrahydrofuran, dimethylformamide, chloroform, dichloromethane, hexamethylphosphoramide, or a mixture of these inert solvents.

When an N-hydroxysuccinimide ester of PPCG is to be reacted with a derivative convertible to 6-APA, the reaction is performed at 0° to 20° C. for one hour to 2 days in the presence of a base such as triethylamine or lutidine in dimethylformamide, dichloromethane, dioxane, or a mixture of these.

When PPCG of formula [V] or its salt or its reactive derivative at the carboxyl group or its derivative having a protected hydroxyl group at the benzene nucleus is to be reacted with a derivative convertible to 6-APA, a reaction product having a moiety of 6-APA and/or PPCG convertible to the penicillin compound of this invention is sometimes formed depending upon the reaction conditions. For example, it is when the carboxyl group of the reaction product is in the form of an ester such as a silyl ester, or when the hydroxyl group at the benzene nucleus of the reaction product is protected by a protective group such as an acyl group. In such a case, the reaction product is hydrolyzed or catalytically hydrogenolyzed in a customary manner known in the chemistry of penicillins to obtain the penicillin compound of this invention.

The penicillin compounds obtained by process (a) or process (b) can be in the form of free carboxylic acid or salt according to the selection of the starting compounds, the reaction conditions, etc. The carboxylic acid is converted to a salt by treatment with a basic substance such as sodium 2-ethylhexanoate, sodium hydroxide, or sodium carbonate. The salt, on the other hand, is treated with an acid substance, if desired, to form a free carboxylic acid.

The isolation, purification, extraction, and recrystallization and other post-treatments of the product are performed in accordance with customary procedures in the chemistry of penicillins.

The starting compound of formula [II] can be obtained intramolecularly cyclizing a compound of the general formula

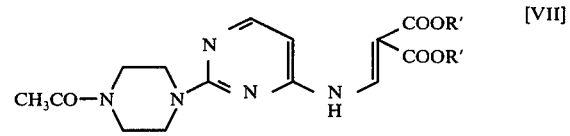

wherein R' is an alkyl group containing 1 to 6 carbon atoms, to form a compound of the general formula

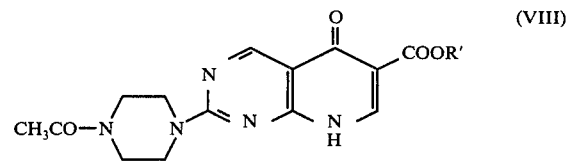

wherein R' is the same as defined above, hydrolyzing the compound [VIII] to form a compound of the formula

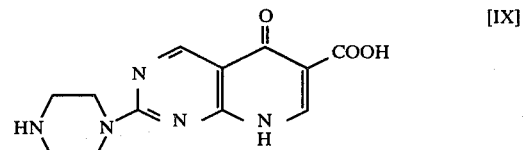

and then formylating or acetylating the compound [IX].

The formylation or acetylation can be performed by suspending the compound of formula [IX] in a formylating agent such as a mixture of acetic anhydride and formic acid or a mixture of formic acid and formamide, or an acetylating agent such as acetic anhydride, and heating it at 60 to 90° C. for 2 to 3 hours.

The 2-AP substituted pyridopyrimidinecarboxylic acid can also be obtained by hydrolyzing the compound of formula [VIII] under mild conditions in a mixture of hydrochloric acid and ethanol for example.

The intramolecular cyclization reaction of converting the compound of formula [VII] to the compound of formula [VIII] and the hydrolysis of converting the compound of formula [VIII] to the compound of formula [IX] can be performed in accordance with the disclosure of U.S. Pat. No. 3,887,557.

The preparation of the novel penicillin compounds of the invention, and their pharmacological activities are described below. The following description consists of five parts.

Part I

References 1 to 9 showing the preparation of the starting compound of formula [II] used in process (a) (References 1 to 7), and the preparation of the starting compound of formula [V] used in process (b) (References 7 and 8).

Part II

Examples 1 to 16 showing the preparation of the novel penicillin compounds of the invention by process (a) and process (b).

Part III

References 10 to 16 showing the preparation of compounds which are outside the scope of the invention but for which no method for preparation has been known. These References serve to evaluate the pharmacological actions of the pencillin compounds of this invention.

Part IV

Example 17 and 18 showing the production of pharmaceuticals using the penicillin compounds of this invention.

Part V

Examples 19 to 24 and Table I to V showing the pharmacological actions of the penicillin compounds of the invention, Amoxicillin (a known antibacterial agent), penicillin derivatives outside the scope of the invention having similar structures to the penicillin compounds of this invention, etc.

At the outset of each of Examples and References in Parts I to III, the outline of the process employed there is shown by a reaction formula.

[Part I] References 1 to 9 showing the process for preparing the starting compounds used in the present invention:-

Reference 1

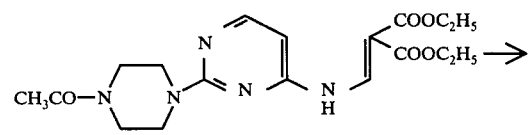

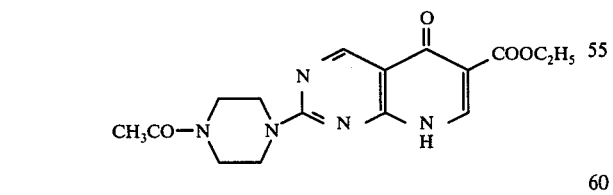

To diphenyl ether (16ml) kept at 250°–255° C. was added with stirring diethyl N-[2-(4-acetyl-1-piperazinyl)-4-pyrimidinyl]-aminomethylenemalonate (2.0g). The mixture was gently refluxed for 10 minutes, and then allowed to cool to room temperature. To the mixture was added n-hexane (12ml). The resulting precipitate was collected, washed with ethanol, and recrystallized from ethanol to yield ethyl 2-(4-acetyl-1-piperazinyl)-5,8-dihydro-5-oxopyrido[2,3-d] pyrimidine-6-carboxylate (1.52 g), m.p. 300°–302° C. (decomp.).

Reference 2

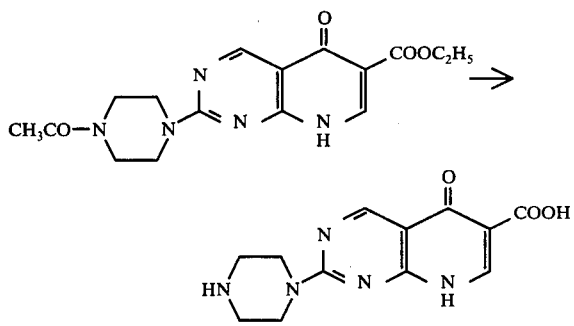

A suspension of ethyl 5,8-dihydro-2-(4-acetyl-1-piperazinyl)-5-oxopyrido[2,3-d]pyrimidine-6-carboxylate (1000 g) and concentrated hydrochloric acid (800 ml) in a mixture of water (1200 ml) and ethanol (1000 ml) was refluxed for 8 hours and allowed to stand overnight. The crystals precipitated were collected, washed with ethanol, and dissolved by heating in an aqueous solution (10 liters) of sodium hydroxide (250 g). The solution was filtered, adjusted to pH 7–8 with acetic acid, and allowed to stand overnight while ice-cooling. The crystalline precipitate was collected, washed with water, and dried at 110° C. to give 5,8-dihydro-2-(1-piperazinyl)-5-oxopyrido[2,3-d] pyrimidine-6-carboxylic acid (625 g). m.p. 299–305° C. (decomp.).

Anal. Calcd. for $C_{12}H_{13}N_5O_3$: C, 52.36; H, 4.76; N, 25.45 Found: C, 52,18; H, 4.63; N, 25.32

Reference 3

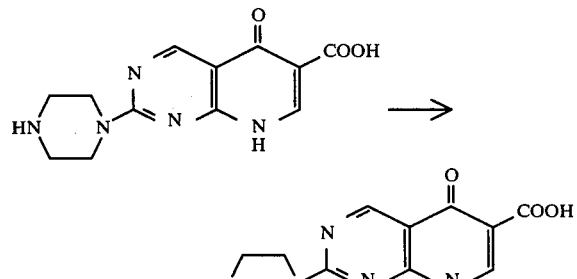

Formic acid (140 ml) was added dropwise to acetic anhydride (200 ml) cooled on an ice bath. The solution was heated at 50° C. for 15 minutes and then cooled to 5° C. To the solution, 5,8-dihydro-2-(1-piperazinyl)-5-oxopyrido[2,3-d] pyrimidine-6-carboxylic acid (70 g) was added. The mixture was heated at 80° C. for 3 hours and then cooled. The crystals precipitated were collected by filtration and washed with ethyl ether to give 5,8-dihydro-2-(4-formyl-1-piperazinyl)-5-oxopyrido[2,3-d]pyrimidine-6-carboxylic acid (75.5 g). m.p. above 300° C.

Anal. Calcd. for $C_{13}H_{13}N_5O_4$: C, 51.48; H, 4.32; N, 23.09 Found: C, 51.41; H, 4.47; N, 23.04

Reference 4

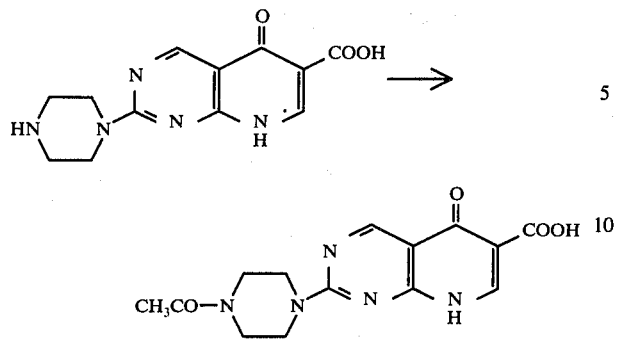

By the same procedure as described in Reference 3, 5,8-dihydro-2-(4-acetyl-1-piperazinyl)-5-oxopyrido[2,3-d] pyrimidine-6-carboxylic acid (933 g) was obtained from 5,8-dihydro-2-(1-piperazinyl)-5-oxopyrido[2,3-d]pyrimidine-6-carboxylic acid (900 g) and acetic anhydride (3200 ml). m.p. 298°–300° C.

Anal. Calcd. for $C_{14}H_{15}N_5O_4$: C, 52.99; H, 4.77; N, 22.07 Found: C, 59.92; H, 4.57; N, 21.91

Reference 5

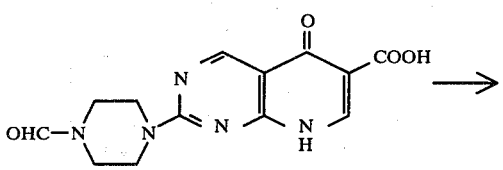

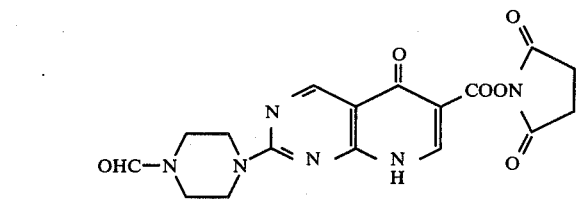

A suspension of 5,8-dihydro-2-(4-formyl-1-piperazinyl)-5-oxopyrido[2,3-d]pyrimidine-6-carboxylic acid (273 g) and triethylamine (299 ml) in dried dichloromethane (3500 ml) was stirred well at room temperature for one hour. To the suspension, isopropyl chloroformate (221 g) was added dropwise with cooling at 0°–10° C. and the reaction mixture was stirred for 2 hours. A solution of N-hydroxysuccinimide (207 g) in dimethylformamide (350 ml) was added to the mixture and the resulting mixture was kept at 5°–10° C. for additional 2 hours. The crystalline product was collected by filtration and washed successively with water (2000 ml) and acetone (2000 ml) to give N-[5,8-dihydro-2-(4-formyl-1-piperazinyl)-5-oxopyrido[2,3-d]pyrimidine-6-carbonyloxy] succinimide (326 g). m.p. above 300° C.

Anal. Calcd. for $C_{17}H_{16}N_6O_6$: C, 51.00, H, 4.03; N, 20.99 Found: C, 50.70; H, 3.89; N, 20.84

Reference 6

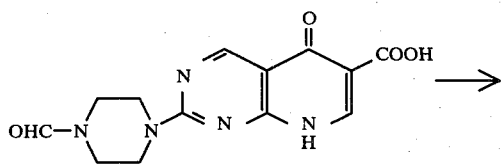

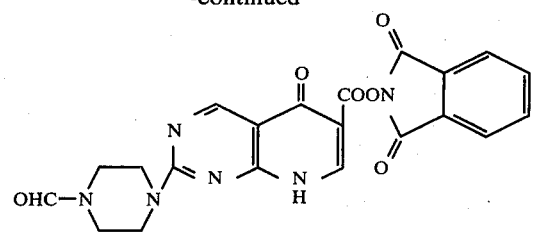

A suspension of 5,8-dihydro-2-(4-formyl-1-piperazinyl)-5-oxopyrido[2,3-d]pyrimidine-6-carboxylic acid (6g) and triethylamine (6.1 ml) in dried dichloromethane (100 ml) was stirred well at room temperature for one hour. To the suspension, ethyl chloroformate (3.8 ml) was added dropwise at 0°–5° C. and the reaction mixture was stirred for one hour at 5°–7° C. The insoluble material was filtered off and to the filtrate was added a solution of N-hydroxyphthalimide (7.19 g) in dimethylformamide (10 ml). The resulting mixture was kept at room temperature for f2 hours. The crystalline product was collected by filtration and washed successively with dichloromethane and acetone to give N-[5,8-dihydro-2-(4-formyl-1-piperazinyl)-5-oxopyrido[2,3-d]pyrimidine-6-carbonyloxy]phthalimide (8.4 g). m.p. 285°–288° C. (decomp.).

Anal. Calcd. for $C_{21}H_{16}O_6N_6$: C, 56.25; H, 3.60; N, 18.74 Found: C, 56.03; H, 3.54; N, 18.59

Reference 7

A suspension of 5,8-dihydro-2-(4-formyl-1-piperazinyl)-5-oxopyrido[2,3-d]pyrimidine-6-carboxylic acid (6 g) and triethylamine (6.1 ml) in dried dichloromethane (100 ml) was stirred well at room temperature for one hour. To the suspension, ethyl chloroformate (3.8 ml) was added at 0°–5° C. and the reaction mixture was stirred for one hour at 5°–7° C. The insoluble material was filtered off and to the filtrate was added a solution of 2,4,6-trichlorophenol (8.68 g) in dichloromethane (30 ml). The reaction mixture was kept at room temperature for 3 hours. The crystalline product was collected by filtration and washed with dichloromethane to give 2,4,6-trichlorophenyl 5,8-dihydro-2-(4-formyl-1-piperazinyl)-5-oxopyrido[2,3-d]pyrimidine-6-carboxylate (8.2). m.p. 285°–290°C. (decomp.).

Anal Calcd. for $C_{19}H_{14}O_4N_5Cl_3$: C, 47.28; H, 2.92, N, 14.51 Found: C, 47.12; H, 3.22; N, 14.72

Reference 8

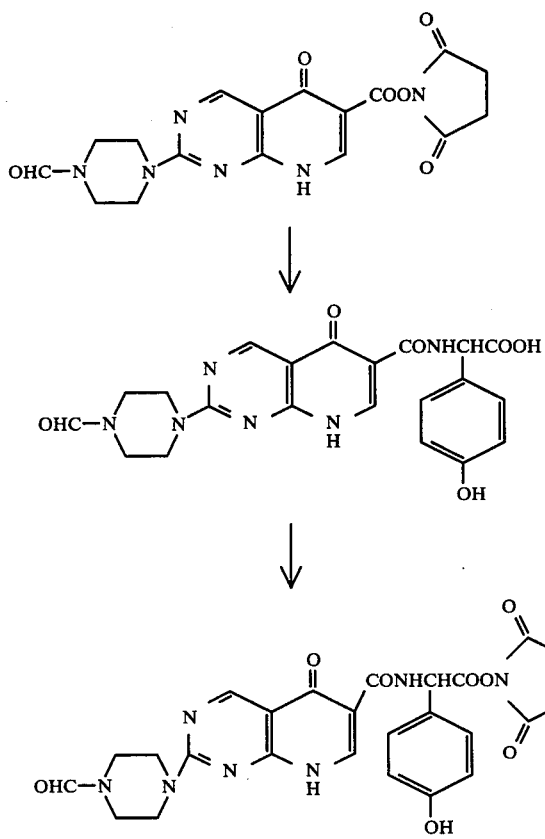

A suspension of D-p-hydroxyphenylglycine (3.3g) and triethylamine (5.6 ml) in dried dimethylformamide (50 ml) was stirred at room temperature for one hour. To the suspension was added N-[5,8-dihydro-2-(4-formyl-1-piperazinyl)-5-oxopyrido[2,3-d]pyrimidine-6-carbonyloxy]succinimide (8.0 g). The mixture was stirred at 5° C. for one hour and then stirred at room temperature for an additional 3 hours. The resulting precipitate was collected and dissolved in ice-water. The aqueous solution was acidified with 10% hydrochloric acid. The crystals precipitated were collected and recrystallized from methanol to give D-α-[5,8-dihydro-2-(4-formyl-1-piperazinyl)-5-oxopyrido[2,3-d]pyrimidine-6-carboxamido]-p-hydroxyphenylacetic acid.

IR (KBr): ν c=O 1710 cm$^{-1}$
NMR (DMSO-d$_6$, δ ):

5.40 (1H, d, J=7Hz 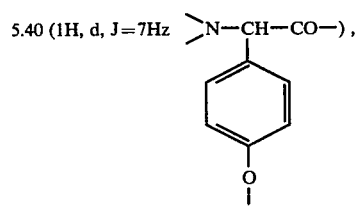

8.12 (1H, s, 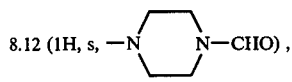

9.12 (1H, s, 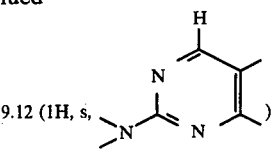 )

Anal. Calcd. for $C_{21}H_{20}N_6O_6 \cdot H_2O$: C, 53.61; H, 4.71; N, 17.87 Found: C, 53.87; H, 4.49; N, 17.55

To a solution of D-α-[5,8-dihydro-2-(4-formyl-1-piperazinyl)-5-oxopyrido[2,3-d]pyrimidine-6-carboxamido]-p-hydroxyphenylacetic acid (9.0 g) and N-hydroxysuccinimide (4.6 g) in dried dimethylformamide (100 ml), dicyclohexylcarbodiimide (5.8 g) was added at −10° C. The mixture was stirred at −10 − 0° C. for one hour and then allowed to stand overnight at room temperature. The precipitate was filtered off and to the filtrate was added ice-water (500 ml). The crystals precipitated were collected and dissolved in acetonitrile (50 ml). The acetonitrile solution was dried over anhydrous magnesium sulfate and concentrated under reduced pressure. The resulting crystals were collected to yield N-{D-α-[5,8-dihydro-2-(4-formyl-1-piperazinyl)-5-oxopyrido[2,3-d]pyrimidine-6-carboxamido]-p-hydroxyphenylacetoxy}succinimide (6 g).

IR (KBr): νC=O 1730, 1780, 1810 cm$^{-1}$
NMR (DMSO-d$_6$, δ):

2.78 (4H, s, 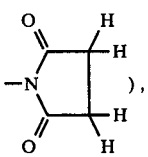 ), 5.92 (1H, d, J=7Hz, 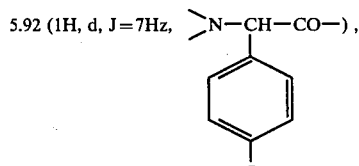, 8.12 (1H, s, 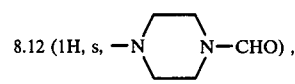, 9.10 (1H, s, 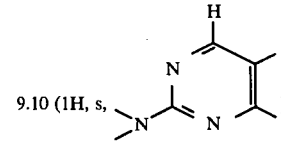 )

Reference 9

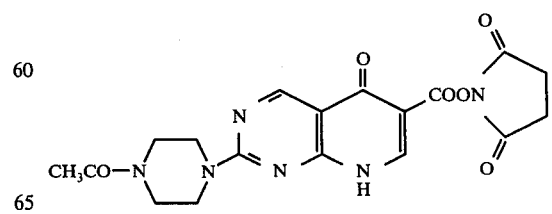

-continued

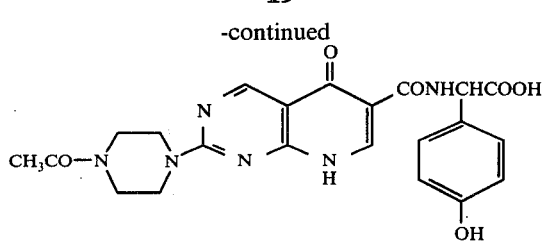

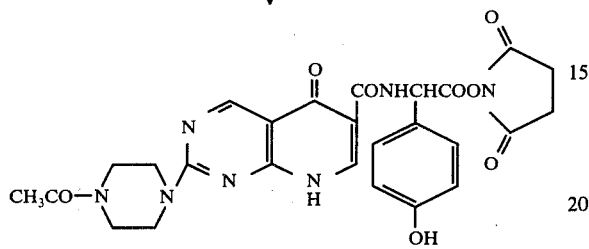

By the same procedure as described in Reference 8, N-{D-α-[5,8-dihydro-2-(4-acetyl-1-piperazinyl)-5-oxopyrido[2,3-d]pyrimidine-6-carboxamido]-p-hydroxyphenylacetoxy}succinimide was obtained from D-p-hydroxyphenylglycine and N-[5,8-dihydro-2-(4-acetyl-1-pyrperazinyl)-5-oxopyrido[2,3-d]pyrimidine-6-carbonyloxy]succinimide.

[Part II] Examples 1 to 16 showing the production of the penicillin compounds [I] of the invention:-

EXAMPLE 1

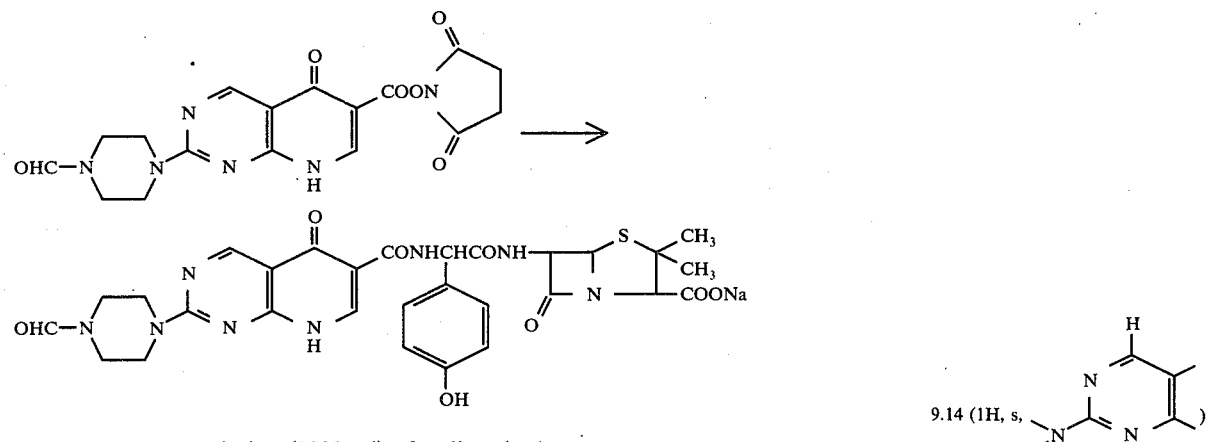

To an aqueous solution (2000 ml) of sodium hydroxide (22 g) was added successively at 0°–2° C. with cooling D-α-amino-p-hydroxybenzylpenicillin (230 g) and N-[5,8-dihydro-2-4-formyl-1-piperazinyl)-5-oxopyrido[2,3-d]pyrimidine-6-carbonyloxy]succinimide (200 g) and the mixture was stirred for a half hour. A 1N sodium hydroxide solution (550 ml) was added to the mixture amd the resulting mixture was kept for an additional one hour, and then filtered. To the filtrate was added ice-water (3000 ml). The solution was adjusted to pH 2 with 10% hydrochloric acid. The resulting precipitate was collected by filtration, washed twice with ice-water (4000 ml) and dissolved in an enough volume of a 4% sodium hydroxide solution to adjust the pH to 6.5. The aqueous solution was filtered and the filtrate was lyophilized to give D-α-[5,8-dihydro-2-(4-formyl-1-piperazinyl)-5-oxopyrido[2,3-d]pyrimidine-6-carboxamido]-p-hydroxybenzyl-penicillin sodium salt (324 g).

IR (KBr): $\nu C=O$ 1760 cm$^{-1}$
NMR (DMSO-d$_6$, δ ):

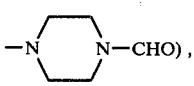

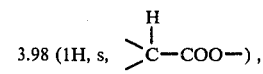

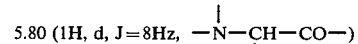

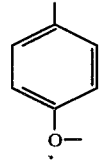

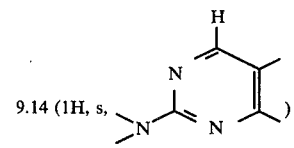

Anal. Calcd. for $C_{29}H_{29}N_8O_8SNa \cdot 2H_2O$: C, 49.15; H, 4.69; N, 15.81; S, 4.53 Found: C, 49.11; H, 4.78; N, 15.75; S, 4.63

EXAMPLE 2

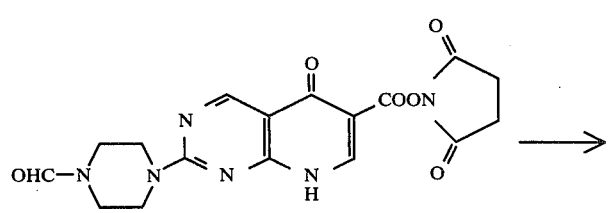

-continued

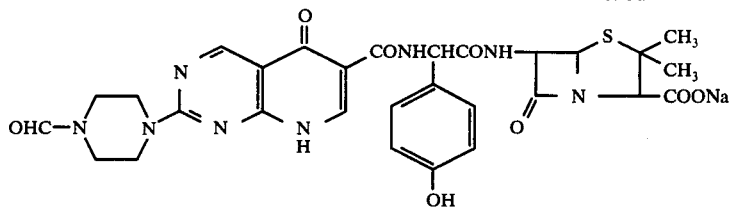

To a solution of D-α-amino-p-hydroxybenzylpenicillin (230 g) and triethylamine (76 ml) in dried dimethylformamide (1000 ml), N-[5,8-dihydro-2-(4-formyl-1-piperazinyl)-5-oxopyrido[2,3-d]pyrimidine-6-carbonyloxy]succinimide (200 g) was added at 0° -2° C. and the reaction mixture was stirred for 1.5 hours. A 30% solution of sodium 2-ethylhexanoate in n-butanol (335 ml) and acetone (7000 ml) was added successively to the mixture. The resulting precipitate was collected by filtration, washed with acetone and dissolved in ice-water. The aqueous solution was acidified with 10% hydrochloric acid and the crystals precipitated were collected, washed well with water and dissolved in a 2% sodium hydroxide solution. The solution was adjusted to pH 6.5 and filtered. The filtrate was lyophilized to give D-α-[5,8-dihydro-2-(4-formyl-1-piperazinyl)-5-oxopyrido[2,3-d]pyrimidine-6-carboxamido]-p-hydroxybenzylpenicillin sodium salt (289 g).

This compound was identified with the compound of Example 1 by comparison of IR and NMR spectra.

EXAMPLE 3 bonyloxy]phthalimide (4.48 g) was added and the reaction mixture was stirred at room temperature for one hour. The insoluble material was filtered off and to the filtrate was added successively a 30% solution of sodium 2-ethylhexanoate in n-butanol (7.3 ml) and acetone (300 ml). The resulting precipitate was collected by filtration, washed with acetone and dissolved in ice-water. The aqueous solution was adjusted to pH 2 with 10% hydrochloric acid. The precipitate was collected, washed with water and dissolved in dimethylformamide (60 ml). The solution was treated with charcoal (1.5 g) and filtered. To the filtrate was added successively a 30% solution of sodium 2-ethylhexanoate in n-butanol (7 ml) and acetone (300 ml). The precipitate was collected and dissolved in ice-water. The aqueous solution was adjusted to pH 2 with 10% hydrochloric acid. The resulting precipitate was collected, washed with water and dissolved in a 2% sodium hydroxide solution to adjust the pH to 6.5. The aqueous solution was filtered and lyophilized to give D-α-[5,8-dihydro-2-(4-formyl-1-piperazinyl)-5-oxopyrido [2,3-d]pyrimidine-6-carboxamido]-p-hydroxybenzylpenicillin sodium salt (4.83 g).

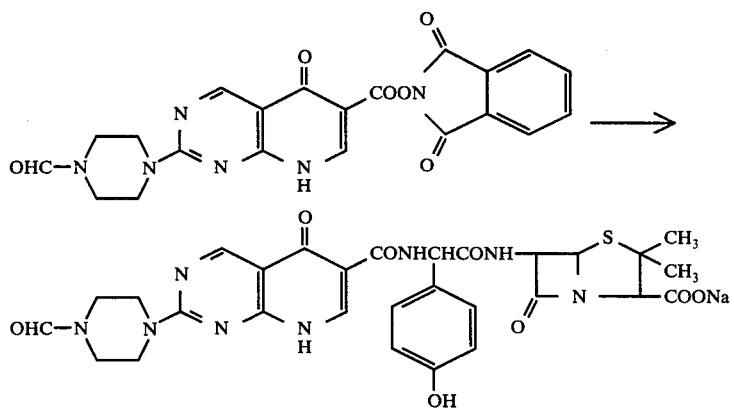

To a solution of D-α-amino-p-hydroxybenzylpenicillin (4.61 g) and triethylamine (1.53 ml) in dried dimethylformamide (30 ml), N-[5,8-dihydro-2-(4-formyl-1-piperazinyl)-5-oxopyrido[2,3-d]pyrimidine-6-car- This compound was identified with the compound of Example 1 by comparison of IR and NMR spectra.

EXAMPLE 4

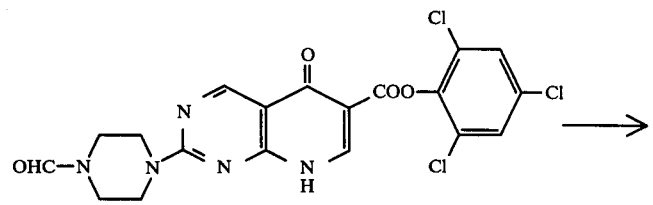

-continued

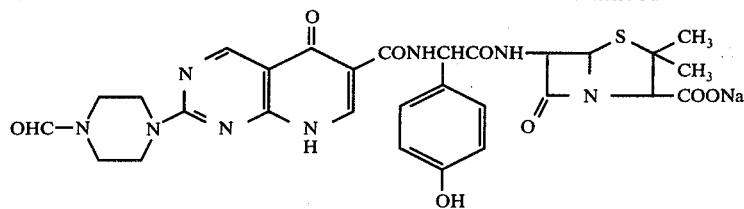

To a solution of D-α-amino-p-hydroxybenzylpenicillin (1.11 g) and triethylamine (0.38 ml) in dried dimethylformamide (10 ml), 2,4,6-trichlorophenyl 5,8-dihydro-2-(4-formyl-1-piperazinyl)-5-oxopyrido[2,3-d]pyrimidine-6-carboxylate (2.16 g) was added and the reaction mixture was stirred at room temperature for 2 days. The insoluble material was filtered off and to the filtrate was added successively a 30% solution of sodium 2-ethylhexanoate in n-butanol (1.5 ml) and acetone (150 ml). The resulting precipitate was collected by filtration, washed with acetone and dissolved in ice-water. The aqueous solution was adjusted to pH 2 with 10% hydrochloric acid. The precipitate was collected, washed with water and dissolved in dimethylformamide. The dimethylformamide solution was treated with charcoal and filtered. To the filtrate was added successively a 30% solution of sodium 2-ethylhexanoate in n-butanol and acetone. The precipitate was collected and dissolved in ice-water. The aqueous solution was adjusted to pH 2 with 10% hydrochloric acid. The precipitate was collected, washed with water and dissolved in a 2% sodium hydroxide solution to adjust the pH to 6.5. The aqueous solution was filtered and lyophilized to give D-α-[5,8-dihydro-2-(4-formyl-1-piperazinyl)-5-oxopyrido[2,3-d]pyrimidine-6-carboxamido]-p-hydroxybenzylpenicillin sodium salt (1.14 g).

This compound was identified with the compound of Example 1 by comparison of IR and NMR spectra.

EXAMPLE 5

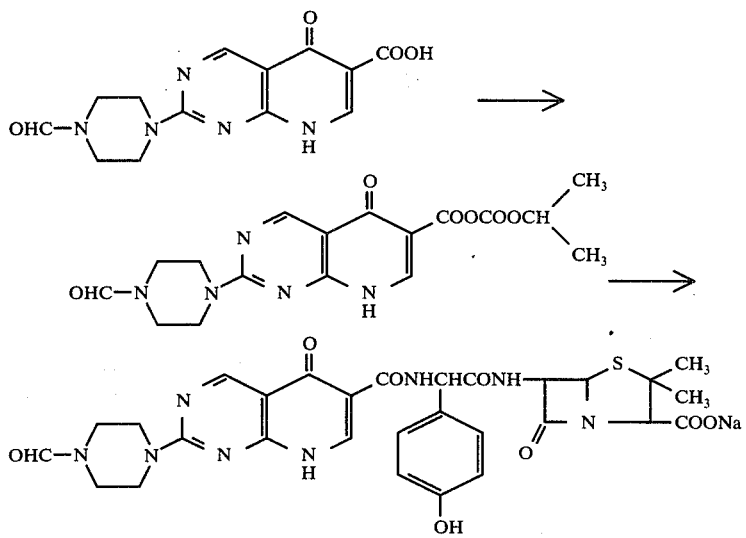

A suspension of 5,8-dihydro-2-(4-formyl-1-piperazinyl)-5-oxopyrido[2,3-d]pyrimidine-6-carboxylic acid (90 g) and triethylamine (42 ml) in dried dichloromethane (1000 ml) was stirred well at room temperature for one hour. Isopropyl chloroformate (36.8 g) was added to the suspension with cooling and the mixture was kept at 5°–7° C. for one hour. A solution of D-α-amino-p-hydroxybenzylpenicillin (126 g) and triethylamine (46 ml) in dried dimethylformamide (350 ml) was added to the mixture. The resulting mixture was stirred at 5°–7° C. for an additional 1.5 hours and allowed to stand overnight at −10° C.

The insoluble material was filtered off and to the filtrate was added successively a 30% sodium 2-ethylhexanoate solution in n-butanol (250 ml) and acetone (3000 ml).

The resulting precipitate was collected by filtration and dissolved in ice-water. The aqueous solution was adjusted to pH 2 with 10% hydrochloric acid. The precipitate was washed with water and dissolved in dimethylformamide (380 ml). After treatment of the solution with charcoal (20 g), a 30% sodium 2-ethylhexanoate solution in butanol (130 ml) and acetone (5000 ml) was added successively to the solution.

The resulting precipitate was collected, washed with acetone and dissolved in ice-water. The aqueous solution was adjusted to pH 2 with 10% hydrochloric acid. The precipitate was collected, washed with water and dissolved in a 2% sodium hydroxide solution to adjust the pH to 6.5. The solution was filtered and lyophilized to give D-α-[5,8-dihydro-2-(4-formyl-1-piperazinyl)-5-oxopyrido[2,3-d]pyrimidine-6-carboxamido]-p-hydroxybenzylpenicillin sodium salt (78.7 g).

This compound was identified with the compound of Example 1 by comparison of IR and NMR spectra.

EXAMPLE 6

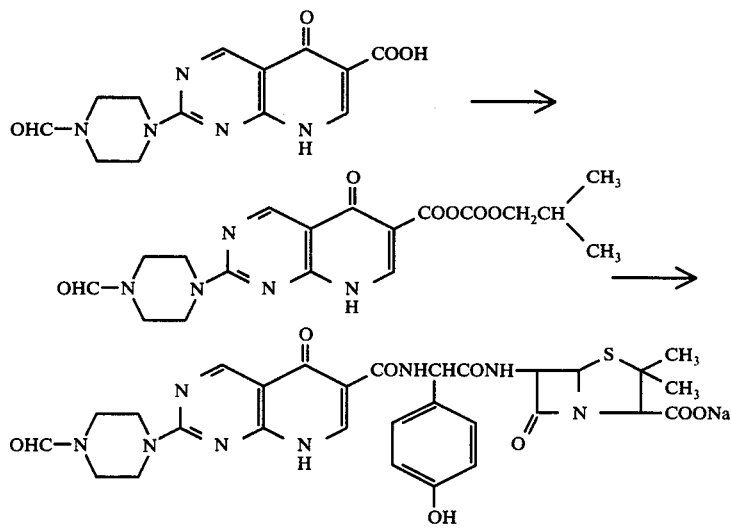

By the same procedure as described in Example 5, D-α-[5,8-dihydro-2-(4-formyl-1-piperazinyl)-5-oxopyrido[2,3-d]pyramidine-6-carboxamido]-p-hydroxybenzylpenicillin sodium salt (155 g) was obtained from 5,8-dihydro-2-(4-formyl-1-piperazinyl)-5-oxopyrido[2,3-d]pyrimidine-6-carboxylic acid (152 g) and isobutyl chloroformate (79 ml).

This compound was identified with the compound of Example 1 by comparison of IR and NMR spectra.

EXAMPLE 7

By the same procedure as described in Example 5, D-α-[5,8-dihydro-2-(4-formyl-1-piperazinyl)-5-oxopyrido[2,3-d]pyrimidine-6-carboxamido]-p-hydroxybenzylpenicillin sodium salt (29 g) was obtained from 5,8-dihydro-2-(4-formyl-1-piperazinyl)-5-oxopyrido[2,3-d]pyrimidine-6-carboxylic acid (30 g) and sec-butyl chloroformate (13.7 g).

This compound was identified with the compound of Example 1 by comparison of IR and NMR spectra.

EXAMPLE 8

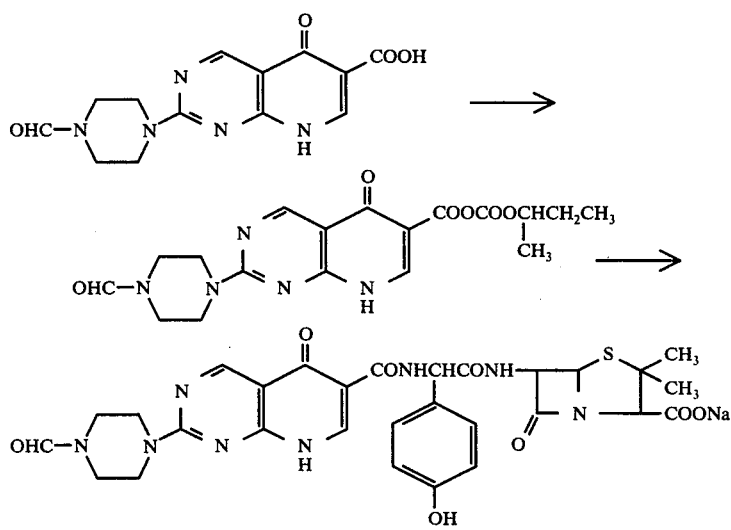

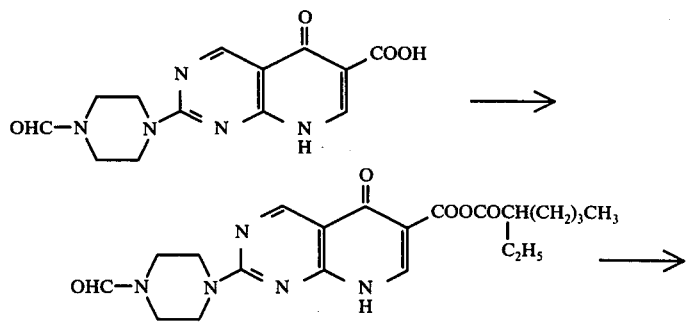

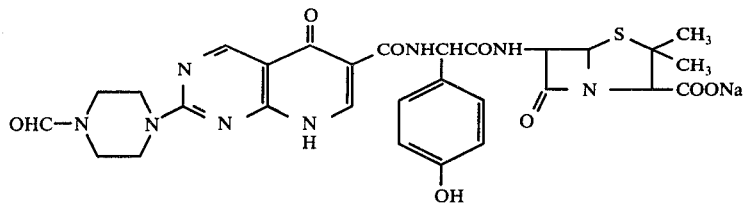

By the same procedure as described in Example 5 except that the reaction was carried out at −10° C., D-α-[5,8-dihydro-2-(4-formyl-1-piperazinyl)-5-oxopyrido[2,3-d]pyrimidine-6-carboxamido]-p-hydroxybenzylpenicillin sodium salt (15 g) was obtained from 5,8-dihydro-2-(4-formyl-1-piperazinyl)-5-oxopyrido[2,3-d]pyrimidine-6-carboxylic acid (30 g) and 2-ethylhexanoyl chloride (19.5 g).

This compound was identified with the compound of Example 1 by comparison of IR and NMR spectra.

EXAMPLE 9

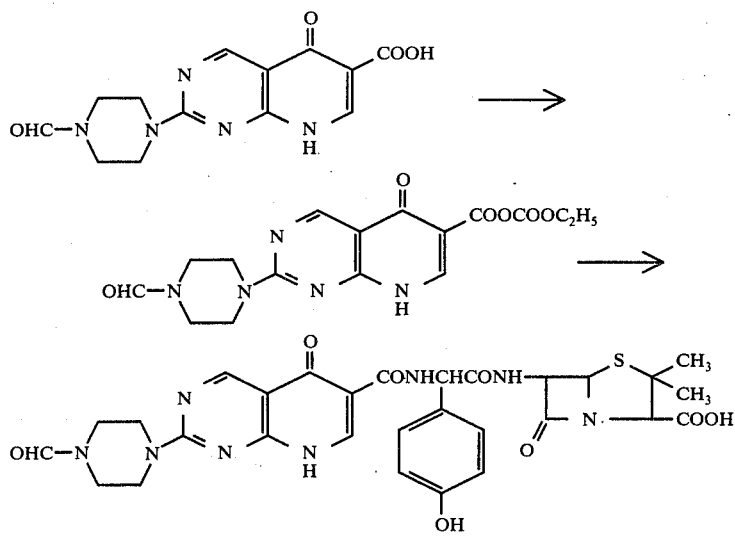

A suspension of 5,8-dihydro-2-(4-formyl-1-piperazinyl)-5-oxopyrido[2,3-d]pyrimidine-6-carboxylic acid (3.0 g) and triethylamine (1.66 ml) in dried dimethylformamide (50 ml) was stirred at room temperature for 30 minutes. To the reaction mixture, ethyl chloroformate (1.14 ml) was added at 5°–10° C. and the mixture was stirred for one hour.

On the other hand, a suspension of D-α-amino-p-hydroxybenzylpenicillin (5.0 g), triethylamine (2.77 ml), and anhydrous magnesium sulphate (2.0 g) in dried dimethylformamide (60 ml) was stirred at room temperature for 30 minutes, and the insoluble material was filtered. The filtrate was added to the preceding suspension at 5°–10° C. and the mixture was stirred for an additional 2 hours. The insoluble material was filtered off and to the filtrate was added a 20% solution of sodium 2-ethylhexanoate in n-butanol (10 ml). Then ethyl ether (500 ml) was added to it. The crystals precipitated were collected and dissolved in water (300 ml). The aqueous solution was acidified with diluted hydrochloric acid. The precipitate was collected, washed with water, and dried to give D-α-[5,8-dihydro-2-(4-formyl-1-piperazinyl)-5-oxopyrido[2,3-d]pyrimidine-6-carboxamido]-p-hydroxybenzylpenicillin (3.4 g).

IR (KBr): $\nu$ C=O 1770 cm$^{-1}$
NMR (DMSO-d$_6$, δ):

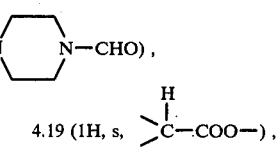

8.10 (1H, s, —N⟨⟩N—CHO), 4.19 (1H, s, >C—COO—),

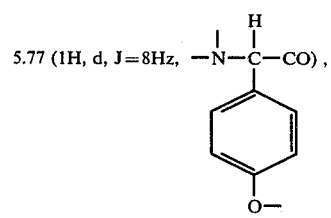

5.77 (1H, d, J=8Hz, —N—C—CO),

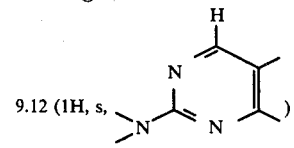

9.12 (1H, s, )

Anal. Calcd. for $C_{29}H_{30}N_8O_8S \cdot 3H_2O$: C, 49.43; H, 5.15; N, 15.90; S, 4.55 Found: C, 49.64; H, 4.91; N, 15.86; S, 4.72

EXAMPLE 10

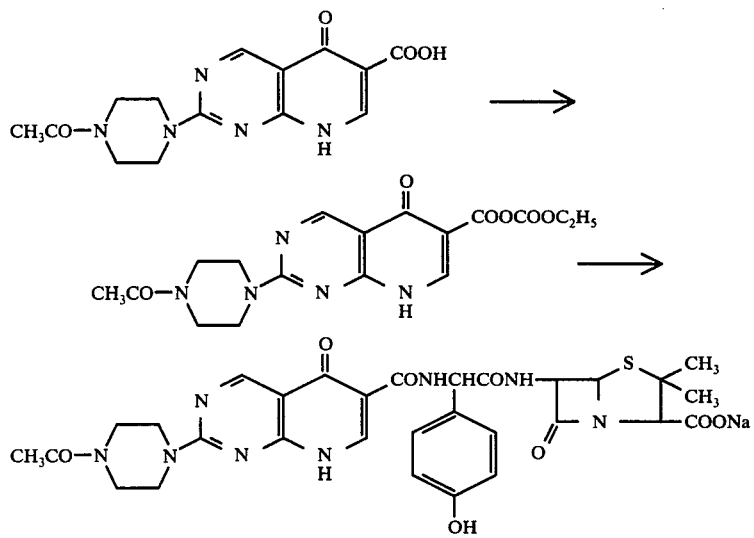

A suspension of 5,8-dihydro-2-(4-acetyl-1-piperazinyl)-5-oxopyrido[2,3-d]pyrimidine-6-carboxylic acid (9.31 g) and triethylamine (4.98 ml) in dried dichloromethane (180 ml) was well stirred at room temperature for one hour. To the suspension, ethyl chloroformate (3.42 ml) was added dropwise with cooling at 3°–5° C. and the mixture was stirred at 3°–8° C. for one hour. To the reaction mixture was added a solution of D-α-amino-p-hydroxybenzylpenicillin (15 g) and triethylamine (7.5 ml) in dried dimethylformamide (120 ml) and the resulting mixture was stirred for 2 hours. The insoluble material was filtered off and to the filtrate was added successively a 20% solution of sodium 2-ethylhexanoate in n-butanol (27 ml) and acetone (1000 ml). The resulting precipitate was collected by filtration and dissolved in ice water. The aqueous solution was adjusted to pH 2 with 10% hydrochloric acid and the precipitate was collected, washed with water and dissolved in dimethylformamide (250 ml). After treatment of the dimethylformamide solution with charcoal, a 20% solution of sodium 2-ethylhexanoate in n-butanol (27 ml) and acetone (1000 ml) was added successively to the solution. The precipitate was collected and dissolved in icewater. The aqueous solution was adjusted to pH 2 with 10% hydrochloric acid. The crystals precipitated were collected, washed with water, dissolved in a 2% sodium hydroxide solution and adjusted to pH 6.5. The solution obtained was filtered and lyophylized to give D-α-[5,8-dihydro-2-(4-acetyl-1-piperazinyl)-5-oxopyrido[2,3-d]pyrimidine-6-barboxamido]-p-hydroxybenzylpenicillin sodium salt (8.5 g).

IR (KBr): $\nu C=O$ 1760 cm$^{-1}$
NMR (DMSO-d$_6$, δ):

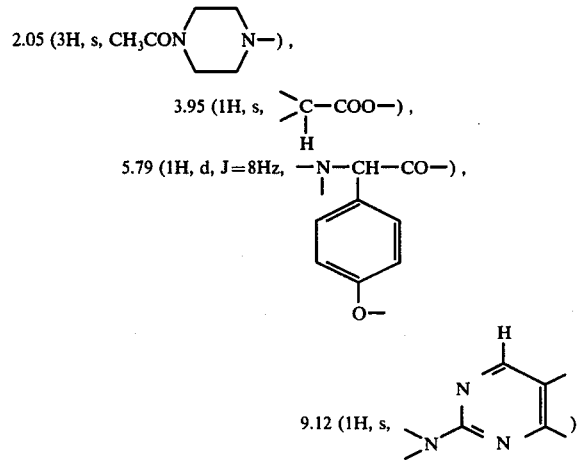

Anal. Calcd. for $C_{30}H_{31}N_8O_8SNa \cdot 4H_2O$: C, 47.49; H, 5.18; N, 14.77; S, 4.23 Found: C, 47.59; H, 4.95; N, 14.56; S, 4.02

EXAMPLE 11

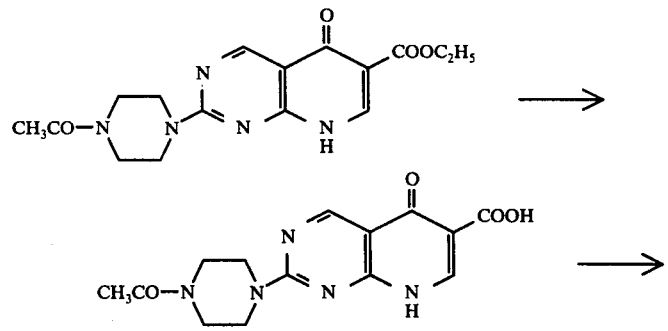

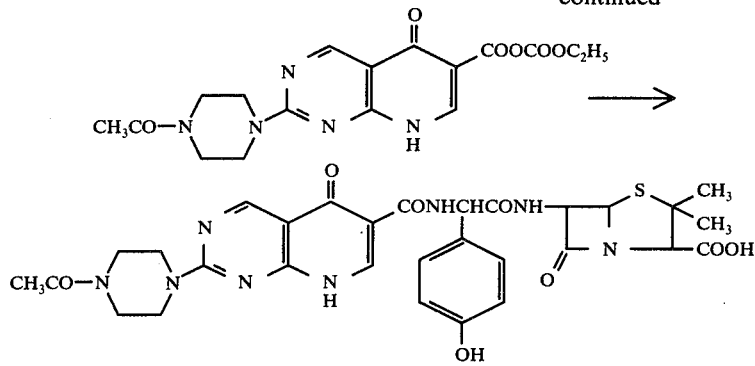

A suspension of ethyl 5,8-dihydro-2-(4-acetyl-1-piperazinyl)-5-oxopyrido[2,3-d]pyrimidine-6-carboxylate (20 g) in a mixture of 4% hydrochloric acid (60 ml) and ethanol (20 ml) was refluxed at 120° C. for 1.5 hours. After cooling, the precipitate was collected, washed with water and then with hot water, and dissolved in a 10% sodium hydroxide solution. The insoluble material was filtered off and the filtrate was acidified with diluted hydrochloric acid. The resulting precipitate was collected and recrystallized from dimethyl sulfoxide to give 5,8-dihydro-2-(4-acetyl-1-piperazinyl)-5-oxopyrido[2,3-d]pyrimidine-6-carboxylic acid (10 g). m.p. 298°–300° C.

A suspension of 5,8-dihydro-2-(4-acetyl-1-piperazinyl)-5-oxopyrido[2,3-d]pyrimidine-6-carboxylic acid (1.57 g) and triethylamine (0.73 ml) in dried dimethylformamide (20 ml) was stirred at room temperature for 30 minutes. To the reaction mixture, ethyl chloroformate (0.5 ml) was added at −5° to −10° C. and the mixture was stirred for one hour.

On the other hand, a suspension of D-α-amino-p-hydroxybenzylpenicillin (2.10 g), triethylamine (1.05 ml) and anhydrous magnesium sulfate (1.0 g) in dried dimethylformamide (20 ml) was stirred at room temperature for 30 minutes, and the insoluble material was filtered off. The filtrate was added to the preceding suspension at −5 to −10°. C. and the mixture was stirred for an additional 2 hours. The insoluble material was filtered off and to the filtrate was added a 20% solution of sodium 2-ethylhexanoate in n-butanol (7.5 ml), and then ethyl ether (200 ml) was added to it. The crystals precipitated were collected and dissolved in a sodium bicarbonate solution. The aqueous solution was acidified with diluted hydrochloric acid and the precipitate was collected, washed with water and dried to give D-α-[5,8-dihydro-2-(4-acetyl-1-piperazinyl)-5-oxopyrido[2,3-d]pyrimidine-6-carboxamido]-p-hydroxybenzylpenicillin (1.35 g).

IR (KBr): $\nu$ C=O 1770 cm$^{-1}$
NMR (DMSO-d$_6$, $\delta$):

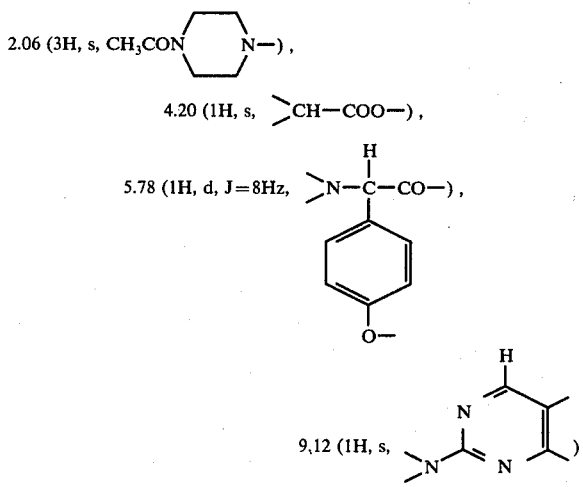

Anal. Calcd. for $C_{30}H_{32}N_8O_8S\cdot 4H_2O$: C, 48.91; H, 5.47; N, 15.21; S, 4.35 Found: C, 48.81; H, 4.99; N, 14.78; S, 4.19

EXAMPLE 12

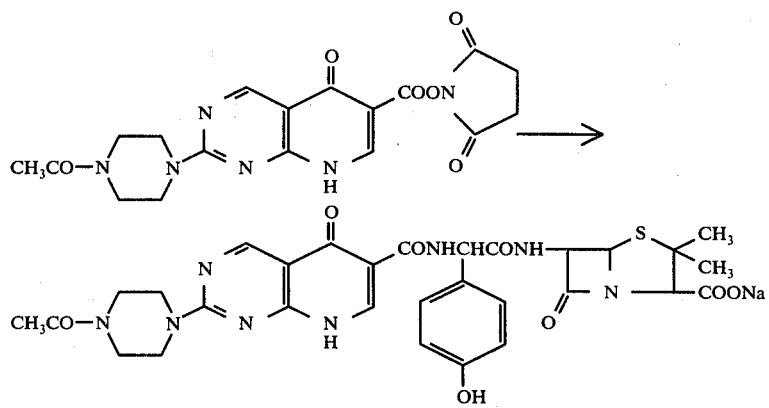

By the same procedure as described in Example 1, D-α-[5,8-dihydro-2-(4-acetyl-1-piperazinyl)-5-oxopyrido[2,3-d]pyrimidine-6-carboxamido]-p-hydroxybenzylpenicillin sodium salt was obtained from D-α-amino-p-hydroxybenzylpenicillin and N-[5,8-dihydro-2-(4-acetyl-1-piperazinyl)-5-oxopyrido[2,3-d]pyrimidine-6-carbonyloxy]succinimide.

This compound was identified with the compound of Example 10 by comparison of IR and NMR spectra.

EXAMPLE 13

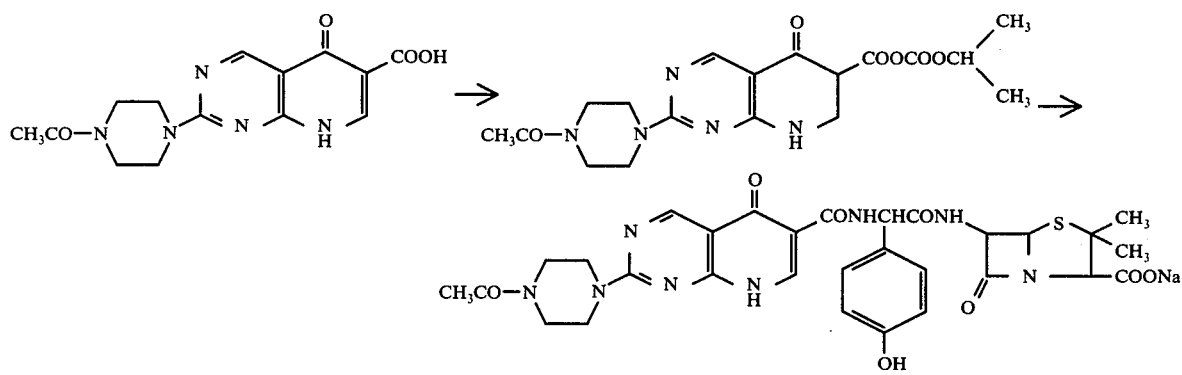

By the same procedure as described in Example 5, D-α-[5,8-dihydro-2-(4-acetyl-1-piperazinyl)-5-oxopyrido[2,3-d]pyrimidine-6-carboxamido]-p-hydroxybenzylpenicillin sodium salt was obtained from 5,8-dihydro-2-(4-acetyl-1-piperazinyl)-5-oxopyrido[2,3-d]pyrimidine-6-carboxylic acid and isopropyl chloroformate.

This compound was identified with the compound of Example 10 by comparison of IR and NMR spectra.

EXAMPLE 14

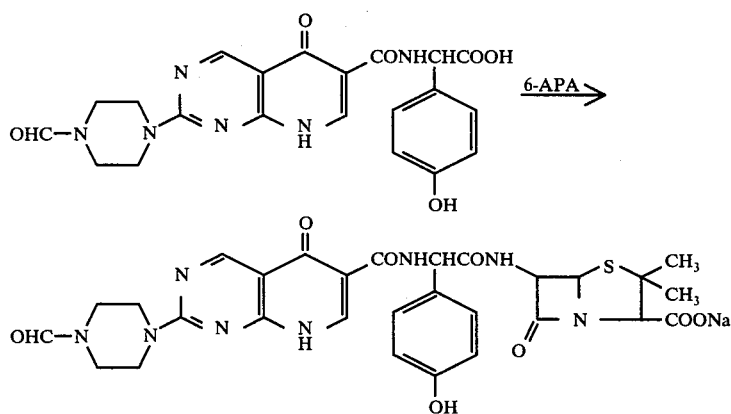

A suspension of 6-aminopenicillanic acid (0.43 g) and N,O-bis(trimethylsilyl)acetamide (0.5 ml) in dried dimethylformamide (10 ml) was stirred at room temperature for a half hour. To the resulting solution, D-α-[5,8-dihydro-2-(4-formyl-1-piperazinyl)-5-oxopyrido[2,3-d]pyrimidine-6-carboxamido]-p-hydroxyphenylacetic acid (0.9 g) was added and the mixture was cooled on an ice bath. To the mixture, dicyclohexylcarbodiimide (0.6 g) was added. The reaction mixture was kept at 0°-5° C. for one hour and then allowed to stand at room temperature for 3 hours. The precipitate was filtered off and to the filtrate was added ice-water (50 ml). The aqueous solution was adjusted to pH 2 with 10% hydrochloric acid. The precipitate was collected and dissolved in a 3% sodium bicarbonate solution. The insoluble material was filtered off and the filtrate was adjusted to pH 2 with 10% hydrochloric acid while cooling. The precipitate was collected, washed with water and dissolved in a 2% sodium hydroxide solution. The aqueous solution was adjusted to pH 6.5, filtered and lyophilized to give D- and L-α-[5,8-dihydro-2-(4-formyl-1-piperazinyl)-5-oxopyrido[2,3-d]pyrimidine-6-carboxamido]-p-hydroxybenzylpenicillin sodium salt.

$[\alpha]_D^{25} = +130°$ C. (C=1, H$_2$O),

IR (KBr): $\nu$ C=0 1760 cm$^{-1}$
NMR (DMSO-d$_6$, δ):

3.99 (s, —CH—COO—, D-form), 4.00 (s, —CH—COO—, L-form), 5.81 (d, J=8Hz, —N—CH—CO—, D-form),

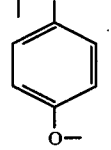

5.74 (d, J=8Hz, —N—CH—CO—, L-form),

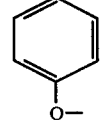

8.11 (s, —NN—CHO, D- and L-form),

-continued

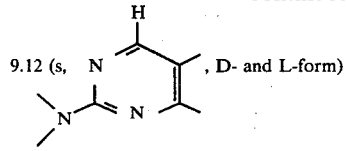

9.12 (s, , D- and L-form)

EXAMPLE 15

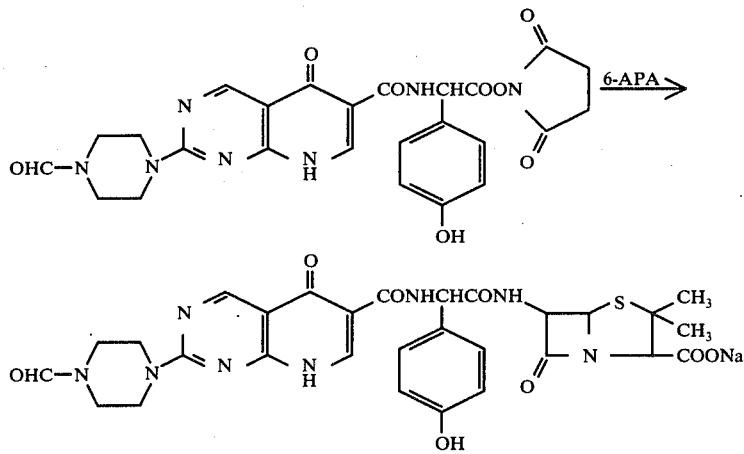

To a mixture of 6-aminopenicillanic acid (0.65 g) and trimethylsilylchloride (0.76 ml) in dried dichloromethane (20 ml), triethylamine (0.83 ml) was added at 0-5° C. and the mixture was stirred at 0°–5° C. for a half hour. To the mixture was added N-{D-α-[5,8-dihydro-2-(4-formyl-1-piperazinyl)-5-oxopyrido[2,3-d]pyrimidine-6-carboxamido]-p-hydroxyphenylacetoxy}succinimide (1.1 g) and triethylamine (0.3 ml).

The mixture was stirred at 0°–10° C. for one hour and then allowed to stand overnight at room temperature. The reaction mixture was extracted with a 3% sodium bicarbonate solution and the extract was adjusted to pH 2 with 10% hydrochloric acid.

The precipitate was collected and dissolved in a small amount of dimethylformamide. A 30% sodium 2-ethylhexanoate solution (1 ml) and then acetone (50 ml) were added to the solution. The precipitate was collected and dissolved in ice-water. The aqueous solution was adjusted to pH 2 with 10% hydrochloric acid. The precipitate was collected, washed with water and dissolved in a 2% sodium hydroxide solution. The solution was adjusted to pH 6.5, filtered and lyophilized to give D- and L-α-[5,8-dihydro-2-(4-formyl-1-piperazinyl)-5-oxopyrido[2,3-d]pyrimidine-6-carboxamido]-p-hydroxybenzylpenicillin sodium salt.

This compound was identified with the compound of Example 14 by comparison of IR and NMR spectra.

EXAMPLE 16

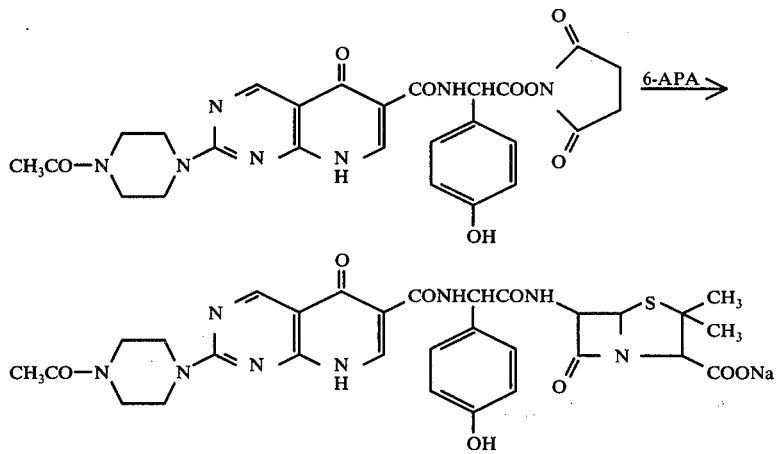

By the same procedure as described in Example 15, D- and L-α-[5,8-dihydro-2-(4-acetyl-1-piperazinyl)-5-oxopyrido[2,3-d]pyrimidine-6-carboxamido]-p-hydroxybenzylpenicillin sodium salt was obtained from 6-aminopenicillanic acid and N-{D-α-[5,8-dihydro-2-(4-acetyl-1-piperazinyl)-5-oxopyrido[2,3-d]pyrimidine-6-carboxamido]-p-hydroxyphenylacetoxy}succinimide.
[Part III]

The following References 10 to 16 show the preparation of compounds outside the scope of the invention whose preparation has not yet been published, in order to evaluate the pharmacological actions of the novel penicillin compounds of the invention.
Reference 10

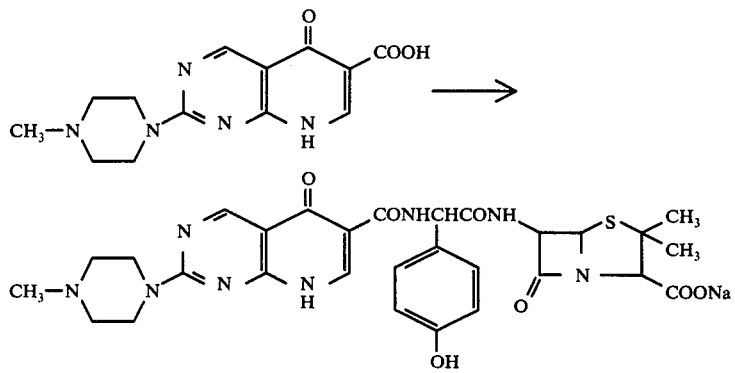

By the same procedure as described in Example 5, D-α-[5,8-dihydro-2-(4-methyl-1-piperazinyl)-5-oxopyrido[2,3-d]pyrimidine-6-carboxamido]-p-hydroxybenzylpenicillin sodium salt was obtained from 5,8-dihydro-2-(4-methyl-1-piperazinyl)-5-oxopyrido[2,3-d]pyrimidine-6-carboxylic acid and D-α-amino-p-hydroxybenzylpenicillin.

IR (KBr): ν C=0 1760 cm$^{-1}$
NMR (DMSO-d$_6$, δ):

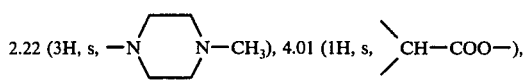
2.22 (3H, s, —N⌒N—CH$_3$), 4.01 (1H, s, \CH—COO—),

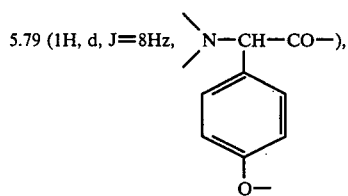
5.79 (1H, d, J=8Hz, \N—CH—CO—),

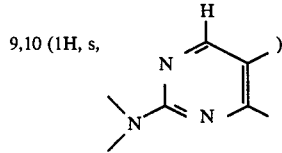
9,10 (1H, s, )

Anal. Calcd. for C$_{29}$H$_{31}$N$_8$O$_7$SNa·4H$_2$O: C, 47.67; H, 5.38; N, 15.33; S, 4.39 Found: C, 47.95; H, 4.96; N, 15.19; S, 4.53
Reference 11

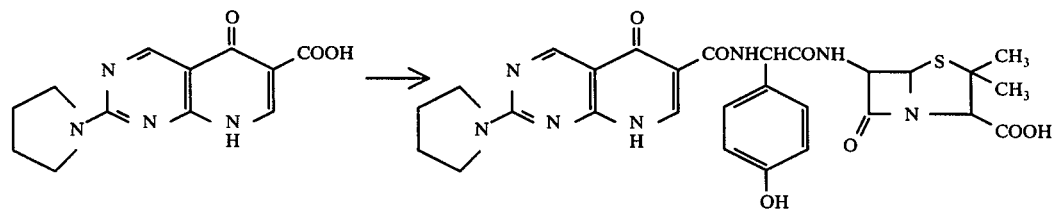

To a suspension of 5,8-dihydro-2-pyrrolidino-5-oxopyrido[2,3-d]pyrimidine-6-carboxylic acid (1.29 g) and triethylamine (0.73 ml) in a mixture of dried hexamethylphosphoramide (25 ml) and dried dichloromethane (5 ml) was added ethyl chloroformate (0.5 ml) at −8° to −10° C. and the mixture was stirred for one hour at −8° to 0° C. To the mixture then was added at 0°–10° C. a solution of D-α-amino-p-hydroxybenzylpenicillin (2.10 g) and triethylamine (1.0 ml) in a mixture of hexamethylphosphoramide (20 ml) and dichloromethane (10 ml), and the mixture was stirred for one hour. After addition of dichloromethane (40 ml) and ice-water, the mixture was adjusted to pH 2 with 10% hydrochloric acid. The organic layer was separated, washed with water, and extracted with a saturated sodium bicarbonate solution. The extract was adjusted to pH 1.5 with 10% hydrochloric acid. The precipitate was collected by filtration, washed with water, and dried to give D-α-[5,8-dihydro-2-pyrrolidino-5-oxopyrido[2,3-d]pyrimidine-6-carboxamido]-p-hydroxybenzylpenicillin (1.6 g).

IR (KBr): νC=0 1770 cm$^{-1}$
NMR (DMSO-d$_6$, δ):

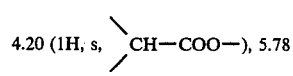
4.20 (1H, s, \CH—COO—), 5.78

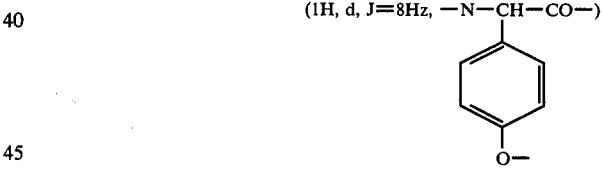
(1H, d, J=8Hz, —N—CH—CO—)

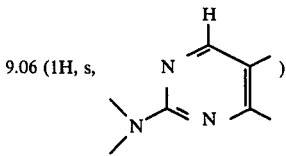
9.06 (1H, s, )

Anal. Calcd. for C$_{28}$H$_{29}$N$_7$O$_7$S·3H$_2$O: C, 50.83; H, 5.33; N, 14.82; S, 4.85 Found: C, 51.07; H, 4.87; N, 15.13; S, 4.79 Reference 12

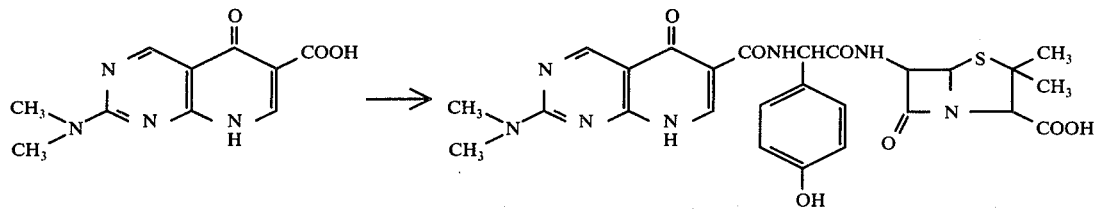

By the same procedure as described in Reference 11, D-α-(5,8-dihydro-2-dimethylamino-5-oxopyrido[2,3-d]pyrimidine-6-carboxamido)-p-hydroxybenzylpenicillin (0.56 g) was obtained from 5,8-dihydro-2-dimethylamino-5-oxopyrido[2,3-d]pyrimidine-6-carboxylic acid (1.18 g) and D-α-amino-p-hydroxybenzylpenicillin (1.58 g).

IR (KBr): $\nu C=O$ 1770 cm$^{-1}$
NMR (DMSO-d$_6$, δ):

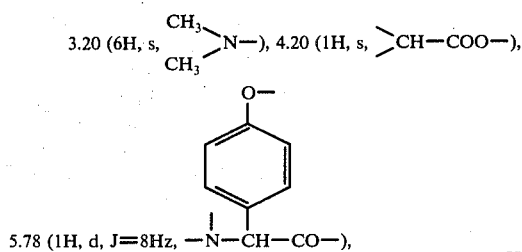

Anal. Calcd. for $C_{26}H_{27}N_7O_7S \cdot 3H_2O$: C, 49.12; H, 5.23; N, 15.42; S, 5.04 Found: C, 48.86; H, 4.82; N, 15.77; S, 5.14

Reference 13 dihydro-5-oxopyrido[2,3-d]pyrimidine-6-carbonyloxy)succinimide (1.9 g) m.p. above 300° C.

To a solution of D-α-amino-p-hydroxybenzylpenicillin (5.54 g) and triethylamine (1.83 ml) in dried dimethylformamide (50 ml), N-(2-amino-5,8-dihydro-5-oxopyrido[2,3-d]pyrimidine-6-carbonyloxy)succinimide (3.65 g) was added at 1°-2° C. and the mixture was stirred at 1°-5° C. for 1.5 hours. The resulting crystals were collected by filtration, washed with dichloromethane and dissolved in ice-water. The aqueous solution was adjusted to pH 2.5 with 10% hydrochloric acid and the precipitate was collected, washed with water, and dissolved in an enough volume of a 2% sodium hydroxide solution to adjust the pH to 7. The solution was filtered and lyophilized to give D-α-(2-amino-5,8-dihydro-5-oxopyrido[2,3-d]pyrimidine-6-carboxamido)-p-hydroxybenzylpenicillin sodium salt (4.0 g).

IR (KBr): $\nu C=O$ 1760 cm$^{-1}$
NMR (DMSO-d$_6$, δ):

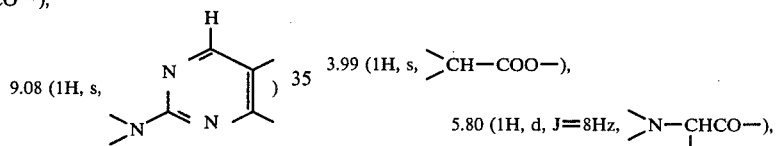

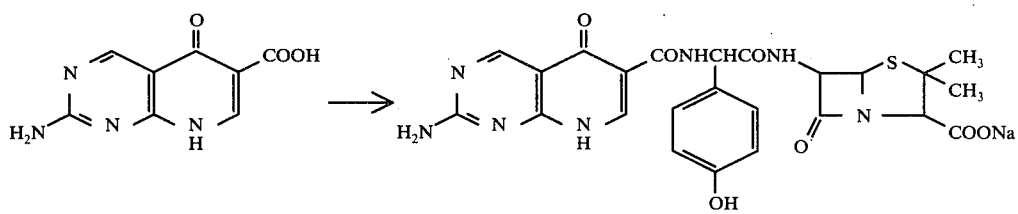

A suspension of 2-amino-5,8-dihydro-5-oxopyrido[2,3-d]pyrimidine-6-carboxylic acid (1.70 g) and triethylamine (2.5 ml) in dried dimethylformamide (50 ml) was stirred at room temperature for 1 hour and to the suspension was added isopropyl chloroformate (1.90 ml) at 0°-5° C. The mixture was stirred at 5°-10° C. for one hour and a solution of N-hydroxysuccinimide (1.91 g) in dimethylformamide (20 ml) was added to it. The mixture was stirred at room temperature for 1.5 hours. The crystals precipitated were collected and washed with dichloromethane to give N-(2-amino-5,8-

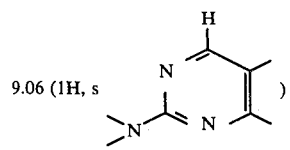

Anal. Calcd. for $C_{24}H_{22}N_7O_7SNa \cdot 5H_2O$: C, 43.30; H, 4.85; N, 14.73; S, 4.82 Found: C, 43.30; H, 4.26; N, 15.14; S, 4.98

Reference 14

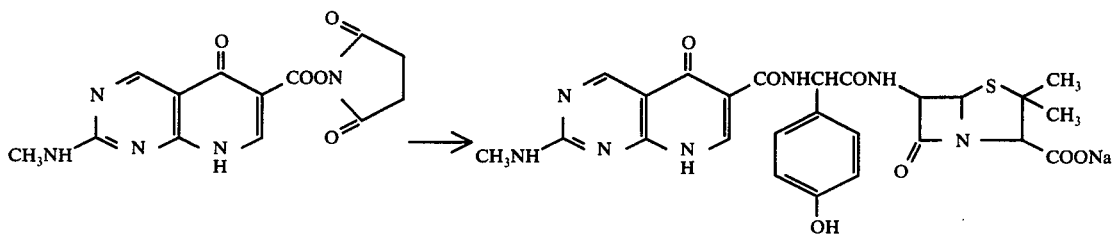

By the same procedure as described in Example 2, D-α-(5,8-dihydro-2-methylamino-5-oxopyrido[2,3-d]pyrimidine-6-carboxamido)-p-hydroxybenzylpenicillin sodium salt (1.6 g) was obtained from D-α-amino-p-hydroxybenzylpenicillin (2.61 g) and N-(5,8-dihydro-2-methylamino-5-oxopyrido[2,3-d]pyrimidine-6-carbonyloxy)succinimide (1.8 g).

IR (KBr): ν C=0 1760 cm$^{-1}$
NMR (DMSO-d$_6$, δ):

2.89 (3H, d, J=4Hz, CH$_3$—N$\langle$ ), 3.96 (1H, s, $\rangle$CH—COO—), 5.81 (1H, d, J=8Hz, $\rangle$N—CH—CO—),

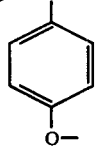

9.06 (1H, broad s, 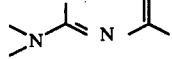 )

Anal. Calcd. for C$_{25}$H$_{24}$N$_7$O$_7$SNa·4H$_2$O: C, 45.38; H, 4.88; N, 14.82; S, 4.85 Found: C, 45.28; H, 4.48; N, 15.35; S, 4.95 Reference 15

By the same procedure as described in Example 1, D-α-[5,8-dihydro-2-(4-formyl-1-piperazinyl)-5-oxopyrido[2,3-d]pyrimidine-6-carboxamido]-benzylpenicillin sodium salt was obtained from N-[5,8-dihydro-2-(4-formyl-1-piperazinyl)-5-oxopyrido[2,3-d]pyrimidine-6-carbonyloxy]succinimide and D-α-aminobenzylpenicillin.

IR (KBr): ν C=0 1760 cm$^{-1}$
NMR (DMSO-d$_6$, δ):

8.11 (1H, s, —N$\diagdown$N—CHO), 3.99 (1H, s, $\rangle$CH—COO—), 5.96 (1H, d, J=8Hz, $\rangle$N—CH—CO—),

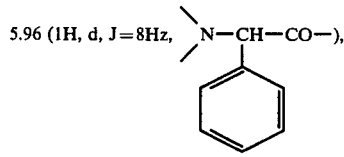

9.15 (1H, s, 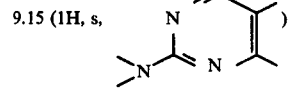 )

Anal. Calcd. for C$_{29}$H$_{29}$N$_8$O$_7$SNa·2H$_2$O: C, 50.28; H, 4.80; N, 16.17; S, 4.63 Found: C, 50.19; H, 4.61; N, 15.91; S, 4.66

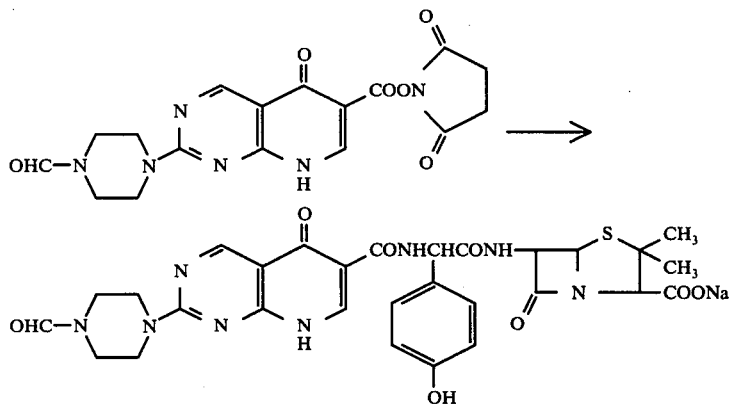

Reference 16

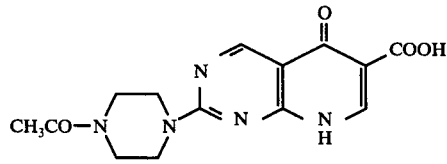

-continued

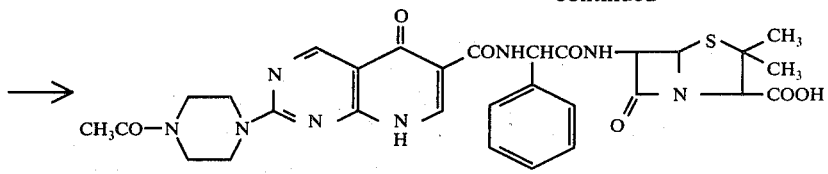

By the same procedure as described in Example 5, D-α-[5,8-dihydro-2-(4-acetyl-1-piperazinyl)-5-oxopyrido[2,3-d]pyrimidine-6-carboxamido]-benzyl-penicillin was obtained from 5,8-dihydro-2-(4-acetyl-1-piperazinyl)-5-oxopyrido[2,3-d]pyrimidine-6-carboxylic acid and D-α-aminobenzylpenicillin.

IR (KBr): $\nu$ C=0 1780 cm$^{-1}$
NMR (DMSO-d$_6$, $\delta$):

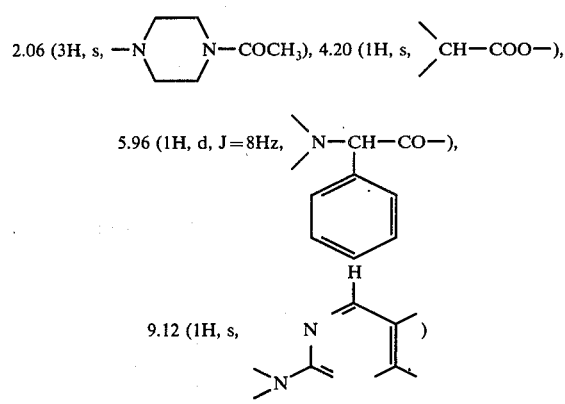

Anal. Calcd. for $C_{30}H_{32}N_8O_7S \cdot 3H_2O$: C, 51.27; H, 5.45; N, 15.95; S, 4.56 Found: C, 51.92; H, 5.15; N, 16.08; S, 4.38

[Part IV]

Examples 17 and 18 showing the production of pharmaceuticals using the penicillin compounds of the invention.

EXAMPLE 17

(1) In an aseptic area, D-α-[5,8-dihydro-2-(4-formyl-1-piperazinyl)-5-oxopyrido[2,3-d]pyrimidine-6-carboxamido]-p-hydroxybenzylpenicillin sodium salt (251 g) was dissolved in 2008 ml of distilled water for injection. The solution was filtered by a Millipore filter (pore size 0.22 micron; product of Millipore Corporation, Bedford, U.S.A.). The solution was poured in an amount of 2.0 ml each into 1000 vials (10 ml capacity), and lyophilized. Each of the vials was then sealed with a rubber stopper and an aluminum cap. Thus, vials (No. A) each containing 250 mg of the active ingredient were obtained.

A physiological saline solution for injections was filled in an amount of 2.0 ml each into ampoules, and sealed to obtain ampoules (No. B). The physiological saline in the ampoules (No. B) was poured into the vials (No. A) to produce injection for intravenous administration.

(2) Distilled water for injections was poured in an amount of 2.0 ml into the vials (No. A), and the solution was dissolved in a 5% solution of glucose for injections (250 ml). Thus, solutions for continual infusion were prepared.

(3) One thousand vials (No.C) each containing 500 mg of D-α-[5,8-dihydro-2-(4-acetyl-1-piperazinyl)-5-oxopyrido[2,3-d]pyrimidine-6-carboxamido]-p-hydroxybenzylpenicillin sodium salt were prepared in the same way as described above except that 502 g of this active ingredient was used.

EXAMPLE 18

(1) In an aseptic area, D-α-[5,8-dihydro-2-(4-formyl-1-piperazinyl)-5-oxopyrido[2,3-d]pyrimidine-6-carboxamido]-p-hydroxybenzylpenicillin sodium salt (251 g) was dissolved in 3012 ml of a physiological saline solution for injections. The solution was filtered by the same Millipore filter as used in Example 17. The resulting solution was poured in an amount of 3.0 ml into each of 1000 borosilicate glass ampoules (5 ml capacity), and sealed. Each of the ampoules contained 250 mg of the active ingredient.

(2) One thousand ampoules each containing 500 mg of D-α-[5,8-dihydro-2-(4-acetyl-1-piperazinyl)-5-oxopyrido[2,3-d]pyrimidine-6-carboxamido]-p-hydroxybenzylpenicillin sodium salt were prepared in the same way as described above except that 502 g of this active ingredient was used.

[Part V]

The following Examples 19 to 24 illustrate the pharmacological activities of the penicillin compounds of this invention in comparison with those of compounds outside the scope of the invention.

Compound 1
D-α-[5,8-Dihydro-2-(4-formyl-1-piperazinyl)-5-oxopyrido[2,3-d]pyrimidine-6-carboxamido]-p-hydroxybenzyl-penicillin sodium salt

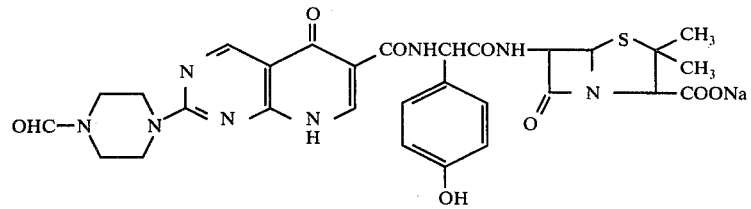

(the compound of this invention)

Compound 2
D-α-[5,8-Dihydro-2-(4-acetyl-1-piperazinyl)-5-oxopyrido[2,3-d]pyrimidine-6-carboxamido]-p-hydroxybenzylpenicillin sodium salt

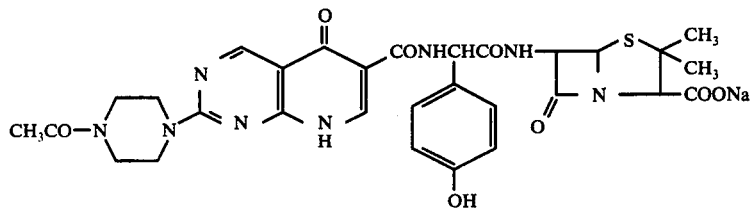

(the compound of this invention)

Compound A
D-α-[5,8-Dihydro-2-(4-methyl-1-piperazinyl)-5-oxopyrido[2,3-d]pyrimidine-6-carboxamido]-p-hydroxybenzylpenicillin sodium salt D-α-[5,8-Dihydro-2-(4-acetyl-1-piperazinyl)-5-oxopyrido[2,3-d]pyrimidine-6-carboxamido]-benzylpenicillin

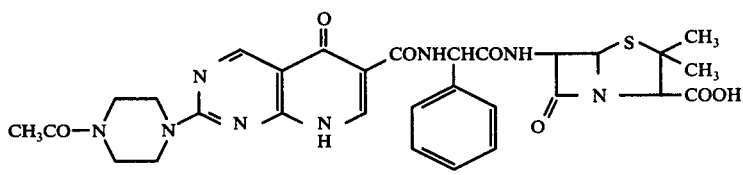

(the compound obtained by Reference 6)

Compound D

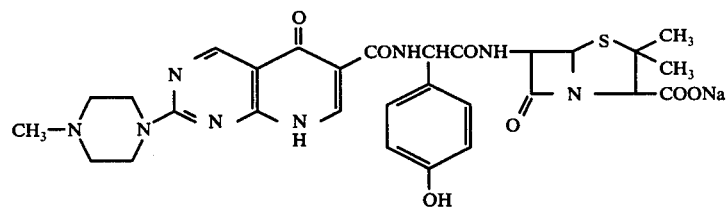

(the compound obtained by Reference 10)

Compound B
D-α-[5,8-Dihydro-2-(4-formyl-1-piperazinyl)-5-oxopyrido[2,3-d]pyrimidine-6-carboxamido]-benzylpenicillin sodium salt D-α-[5,8-Dihydro-2-pyrrolidino-5-oxopyrido[2,3-d]pyrimidine-6-carboxamido]-p-hydroxybenzylpenicillin

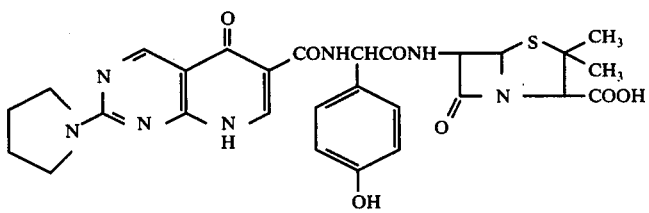

(the compound obtained by Reference 11)

Compound E

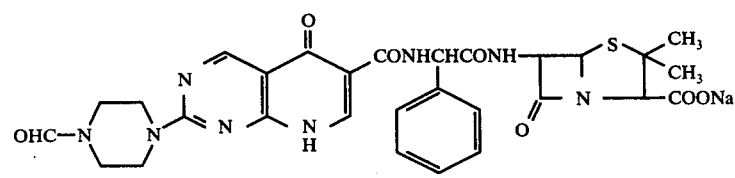

(the compound obtained by Reference 5)

Compound C

D-α-(5,8-Dihydro-2-dimethylamino-5-oxopyrido[2,3-d]pyrimidine-6-carboxamido)-p-hydroxybenzylpenicillin

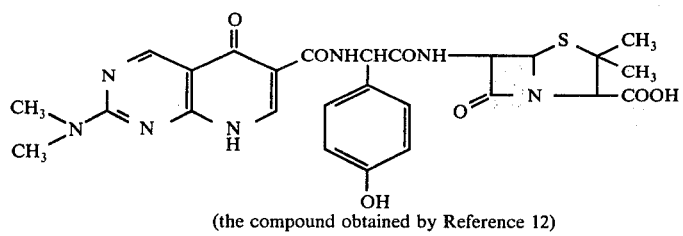

(the compound obtained by Reference 12)

Compound F
D-α-(5,8-Dihydro-2-methylamino-5-oxopyrido[2,3-d]pyrimidine-6-carboxamido)-p-hydroxybenzylpenicillin sodium salt

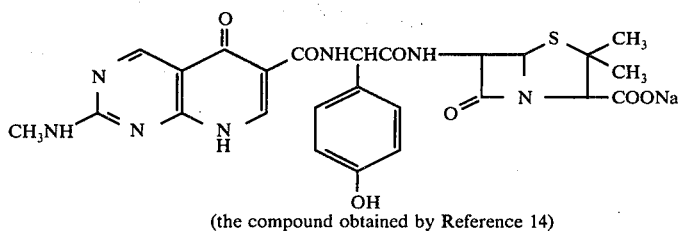

(the compound obtained by Reference 14)

Compound G
D-α-(5,8-Dihydro-2-amino-5-oxopyrido[2,3-d]pyrimidine-6-carboxamido)-p-hydroxybenzylpenicillin sodium salt

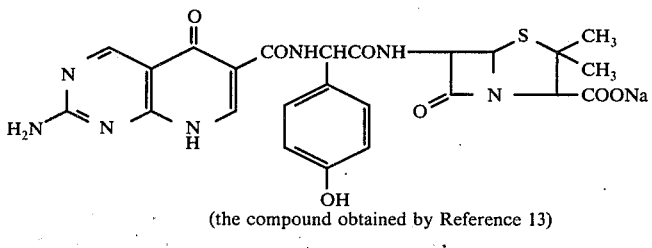

(the compound obtained by Reference 13)

Compound H
D-α-(4-Ethyl-2,3-dioxopiperazine-1-carboxamido)-benzylpenicillin sodium salt (Piperacillin)

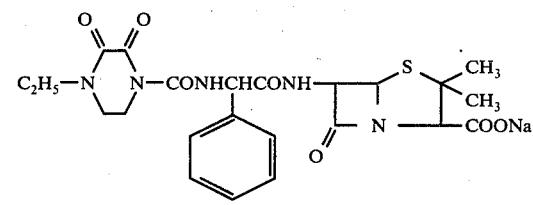

(the compound disclosed in Belgian Patent 828,692)

Compound J
5,8-Dihydro-8-ethyl-2-(1-piperazinyl)-5-oxopyrido[2,3-d]pyrimidine-6-carboxylic acid (Pipenidic acid)

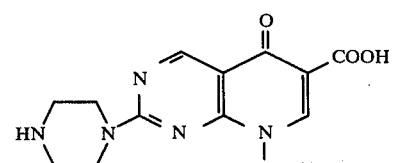

(the compound disclosed in U.S. Pat. No. 3,887,557)

Compound K
5,8-Dihydro-2-(4-formyl-1-piperazinyl)-5-oxopyrido[2,3-d]pyrimidine-6-carboxylic acid

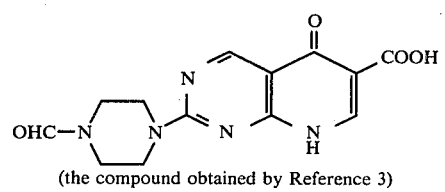

(the compound obtained by Reference 3)

Compound L
5,8-Dihydro-2-(4-acetyl-1-piperazinyl)-5-oxopyrido[2,3-d]pyrimidine-6-carboxylic acid

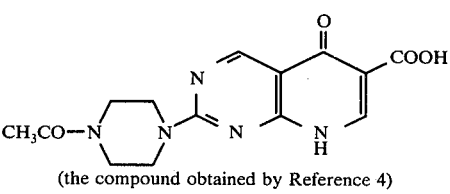

(the compound obtained by Reference 4)

Compound M
D-α-Amino-p-hydroxybenzylpenicillin sodium salt (Amoxicillin)

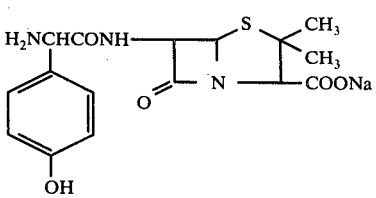

-continued
(the compound disclosed in U.S. Pat. No. 3,674,776)

EXAMPLE 19

The minimum inhibitory concentrations (μg/ml) in vitro are shown in Table I.

EXAMPLE 20 (in vivo efficacy)

The contents in the vials (No. A and No. C) prepared in Example 17 were each dissolved in deionized water, and injections having various concentrations were prepared.

Compounds A, B, F, G, H and M were dissolved in

Table I

| Bacteria | Compound 1 | 2 | A | B | C | D | E | F | G | H | J | K | L | M |
|---|---|---|---|---|---|---|---|---|---|---|---|---|---|---|
| *Staphylococcus aureus* 209P JC-1 | 0.78 | 1.56 | 1.56 | 0.78 | 0.78 | 0.78 | 0.78 | 0.39 | 0.39 | 0.39 | 12.5 | >50 | >50 | 0.1 |
| *Staphylococcus aureus* No. 50774 | 1.56 | 1.56 | 3.13 | 0.78 | 1.56 | 0.78 | 0.78 | 0.39 | 0.39 | 0.78 | 25 | >50 | >50 | 0.1 |
| *Streptococcus faecalis* P-2473 | 3.13 | 6.25 | 6.25 | 6.25 | 12.5 | 6.25 | 3.13 | 1.56 | 1.56 | 3.13 | >200 | >50 | >50 | 0.78 |
| *Streptococcus pyogenes* 65A | 0.006 | 0.006 | <0.1 | <0.1 | <0.1 | <0.1 | 0.025 | <0.1 | <0.1 | 0.025 | >100 | >100 | >100 | 0.025 |
| *Corynebacterium pyogenes* C-21 | 3.13 | 0.78 | 0.78 | 1.56 | 1.56 | 0.78 | 0.78 | 0.78 | 0.78 | 6.25 | 25 | >50 | >50 | 0.39 |
| *Escherichia coli* NIHJ JC-2 | 3.13 | 3.13 | 0.78 | 6.25 | 12.5 | 3.13 | 6.25 | 12.5 | 6.25 | 3.13 | 1.56 | >100 | >100 | 6.25 |
| *Escherichia coli* P-5101 | 1.56 | 0.78 | 0.39 | 3.13 | 3.13 | 1.56 | 1.56 | 3.13 | 3.13 | 1.56 | 3.13 | >100 | >100 | 6.25 |
| *Escherichia coli* P-140a* | 12.5 | 12.5 | 6.25 | 12.5 | 12.5 | 12.5 | 25 | 25 | 50 | 12.5 | 3.13 | >200 | >200 | >200 |
| *Salmonella typhimurium* S-9 | 0.78 | 0.78 | 0.2 | 1.56 | 1.56 | 1.56 | 1.56 | 1.56 | 1.56 | 0.39 | 3.13 | >50 | >50 | 0.78 |
| *Salmonella enteritidis* No. 1891 | 0.78 | 0.78 | 0.2 | 0.78 | 0.78 | 0.39 | 0.78 | 1.56 | 0.78 | 0.39 | 1.56 | >50 | >50 | 0.39 |
| *Shigella flexneri* 2a | 3.13 | 3.13 | 0.78 | 3.13 | 6.25 | 1.56 | 3.13 | 3.13 | 3.13 | 1.56 | 3.13 | >100 | >100 | 6.25 |
| *Shigella flexneri* 4a P-330 | 3.13 | 3.13 | 0.78 | 6.25 | 6.25 | 3.13 | 6.25 | 6.25 | 6.25 | 3.13 | 1.56 | >100 | >100 | 25 |
| *Klebsiella pneumoniae* No. 13 | 12.5 | 12.5 | 6.25 | 6.25 | 12.5 | 6.25 | 12.5 | 25 | 25 | 6.25 | 6.25 | >200 | >200 | 200 |
| *Enterobacter cloacae* P-2540 | 6.25 | 6.25 | 3.13 | 12.5 | 12.5 | 3.13 | 12.5 | 12.5 | 6.25 | 3.13 | 1.56 | >200 | >200 | >200 |
| *Pseudomonas aeruginosa* Tsuchijima | 0.78 | 0.78 | 0.39 | 1.56 | 1.56 | 1.56 | 1.56 | 0.78 | 0.39 | 1.56 | 12.5 | >200 | >200 | 200 |
| *Pseudomonas aeruginosa* No.12 | 3.13 | 3.13 | 1.56 | 6.25 | 6.25 | 3.13 | 3.13 | 6.25 | 3.13 | 3.13 | 25 | >200 | >200 | >200 |
| *Serratia mercescens* IFO 3736 | 6.25 | 6.25 | 3.13 | 12.5 | 12.5 | 6.25 | 6.25 | 12.5 | 12.5 | 0.78 | 6.25 | >100 | >100 | 50 |
| *Proteus morganii* Kono | 6.25 | 6.25 | 3.13 | 3.13 | 6.25 | 6.25 | 6.25 | 12.5 | 6.25 | 0.78 | 3.13 | >200 | >200 | 200 |
| *Proteus rettgeri* P-2503 | 25 | 25 | 6.25 | 6.25 | 12.5 | 6.25 | 6.25 | 12.5 | 6.25 | 1.56 | 6.25 | >100 | >100 | 50 |
| *Proteus mirabilis* P-2381 | 3.13 | 6.25 | 3.13 | 3.13 | 6.25 | 3.13 | 3.13 | 3.13 | 3.13 | 0.78 | 3.13 | >50 | >50 | 1.56 |

Note:
The numerals in the table show minimum inhibitory concentrations (MIC) (μg/ml Method; Chemotherapy 22(6), 1126 (1974)
*Clinically isolated Ampicillin- and Cephalexin-resistant strain The following conclusion can be drawn from Table I.

1. Compounds K and L used as starting compounds in the process of this invention do not substantially show antibacterial activity.

2. Compound J disclosed in U.S. Pat. No. 3,887,557 has inferior antibacterial activity against Gram-positive bacteria such as Staphylococcus aureus, Streptococcus pyogenes and Corynebacterium pyogenes to the penicillin compounds 1 and 2 of this invention.

3. Amoxicillin, an antibacterial agent currently well used and known, which is designated as "Compound M" in Table I (U.S. Pat. No. 3,674,776) is substantially ineffective against Gram-negative pathogenic bacteria, such as Escherichia coli P-140a which is a clinically isolated Ampicillin- and Cephalexin-resistant strain and other Gram-negative bacteria, especially low pathogenic bacteria such as *Klebsiella pneumonia, Enterobacter cloacae, Pseudomonas aeruginosa* and *Serratia marcescens,* whereas the penicillin compounds of this invention show very high antibacterial activities against these bacteria.

deionized water. Compounds C, D, E and J were dissolved in an aqueous solution of sodium carbonate (pH 8–9) to prepare injections of various concentrations.

Each of the injections was administered to mice under the conditions described below, and the median effective doses ($ED_{50}$) obtained are shown in Table II.

Experimental conditions;

| | |
|---|---|
| Mice: | male mice (ddY) weighting about 20g |
| Infection: | *Staphylococcus aureus* No. 50774; Intravenous infection with 50 to 100 $LD_{50}$ (about $5 \times 10^8$ cells/mouse) of a bacterial suspension in saline. *Escherichia coli* P-5101; Intraperitoneal infection with 50 to 100 $LD_{50}$ (about $9 \times 10^6$ cells/mouse) of a bacterial suspension in tryptosoy broth - 4% mucin. *Pseudomonas aeruginosa* No. 12; Intraperitoneal infection with 50 to 100 $LD_{50}$ (about $5 \times 10^3$ cells/mouse) of a bacterial suspension in tryptosoy broth - 4% mucin |
| Medication: | twice, about 5 minutes and 6 hours after infection. |
| Observation: | *Staphylococcus aureus* No. 50774  14 days |

-continued

Experimental conditions;

Eschericha coli  
Pseudomonas aeruginosa No. 12 } 7 days

Table II

| | In vivo efficacy against systemic infection. | | | | |
|---|---|---|---|---|---|
| Bacterium | Staphyloccus aureus No 50774 | Escherichia coli P-5101 | | Pseudomonas aeruginosa No 12 | |
| Route Compound | sc | sc | iv | sc | iv |
| 1 | 2.1 | 3.7 | 2.9 | 2.1 | 4.1 |
| 2 | 3.3 | 4.6 | 3.9 | 5.0 | 6.0 |
| A | 3.7 | 1.0 | 0.7 | 3.6 | 2.6 |
| B | 3.4 | 21.0 | — | 17.7 | — |
| C | — | — | — | >50 | — |
| D | about 10 | 8.6 | — | 38.6 | — |
| E | about 10 | 11.0 | — | 32.4 | — |
| F | about 0.7 | 6.3 | 12.0 | 4.8 | 5.7 |
| G | about 0.8 | 11.5 | 8.8 | 4.4 | 3.9 |
| H | 8.8 | 26.3 | 43.3 | 141.0 | >100 |
| J | >50 | 6.3 | 4.6 | 37.7 | 42.7 |
| M | 0.34 | 3.4 | 3.2 | >200 | — |

Note;
The numerals in the table show $ED_{50}$ (mg/kg). $ED_{50}$ values were calculated in accordance with the Behrens-Kaerber method [Arch. Exp. Path. Pharm., 162, 480 (1931)].
sc: subcutaneous administration
iv: intravenous administration The following conclusion can be drawn from Table II.

1. Compounds 1 and 2 of this invention exhibit excellent antibacterial activity in vivo.

2. Compounds 1 and 2 of this invention have especially high antibacterial activity against Pseudomonas aeruginosa, and have $ED_{50}$ value of 2 to 6 mg/kg in parenteral administration.

3. The antibacterial activities against Pseudomonas aeruginosa of compounds 1 and 2 of this invention in parenteral administration is about 3 to 25 times as high as those of compounds B and C which are Ampicillin derivatives having the same pyridopyrimidinecarboxylic acid residue as in the compounds of this invention.

4. The antibacterial activities against Pseudomonas aeruginosa of compounds 1 and 2 of this invention in parenteral administration are about 6 to 20 times as high as those of compounds D and E which are penicillin compounds resulting from the substitution of the 2-position of the pyridopyrimidine moiety of the compounds 1 and 2 by a 1-pyrrolidinyl or dimethylamino group instead of the 4-substituted-1-piperazinyl group.

5. Compounds 1 and 2 of this invention have far superior antibacterial activity against Pseudomonas aeruginosa in parenteral administration to compound J (Pipemidic acid known as a pharmaceutical having activity especially against Pseudomonas aeruginosa) and compound H (Piperacillin).

EXAMPLE 21 (acute toxicity)

Injections containing compounds 1 and 2 and compounds A to J in various concentrations which were prepared in Example 20 were administered to male mice (ddY) (4 to 8 in each group) in a dose of 0.1 ml per 10g of body weight. The number of dead mice was counted after a lapse of 7 days, and the value of madian lethal dose ($LD_{50}$,mg/kg) was calculated. The results are shown in Table III.

The ratio of $LD_{50}$ to $ED_{50}$ on Pseudomonas aeruginosa No. 12 in Table II, namely a chemotherapeutic index, was calculated, and the results are shown also in Table III.

Table III

| | Acute toxicity in mice. | | |
|---|---|---|---|
| Compound No. | Route | $LD_{50}$ (mg/kg) | Chemotherapeutic Index ($LD_{50}/ED_{50}$) |
| 1 | sc | >6000 | >3000 |
| | iv | 4518 | 1102 |
| 2 | sc | >6000 | >1200 |
| | iv | 4518 | 753 |
| A | sc | 1500 | 417 |
| | iv | 1123 | 432 |
| B | sc | <4000 | >226 |
| | iv | 2828 | — |
| C | sc | >2000 | * |
| | iv | >2000 | — |
| D | sc | <1000 | <23 |
| | iv | <1000 | — |
| E | sc | 1072 | 33 |
| F | sc | 1414 | 295 |
| | iv | 1414 | 248 |
| G | sc | 1000 | 227 |
| | iv | 1000 | 256 |
| H | sc | >6000 | >42 |
| | iv | >4000 | * |
| J | sc | 2244 | 60 |
| | iv | 707 | 17 |

Note:
The $LD_{50}$ values were calculated in accordance with the Behrens-Kaerber method.
* The asterisks in the table show that calculation was impossible.

The following conclusion can be drawn from Table III.

1. The $LD_{50}$ values of compounds 1 and 2 of this invention are about 2 to 10 times as high as those of compounds A to G, and therefore have very high safety.

2. The antibacterial activities in vivo of compounds A resulting from the introduction of a methyl group instead of R in formula (I), and compounds F and G resulting form the substitution of the 2-position of the pyridopyrimidine moiety of the penicillin compound of this invention by a methylamino or amino group are almost comparable those of the penicillin compounds of this invention as shown in Table II, but their $LD_{50}$ values are about ½ to 1/6 of the latter.

3. The $LD_{50}$ value of compound H is almost the same as those of compounds 1 and 2 of this invention, but antibacterial activity in vivo of compound H is only about one-twentieth to one-seventieth of those of the penicillin compounds of this invention as shown in Table II.

4. The chemotherapeutic indices of compounds 1 and 2 of this invention are about 3 to 100 times as high as those of compounds B, D, E, F, G and J. This shows that the penicillin compounds of this invention have excellent antibacterial activity against Pseudomonas aeruginosa.

Example 22 (subacute toxicity)

The contents of the vials No. A and C obtained in Example 17 and the compound A were dissolved in deionized water. Each of the solutions obtained was administered to ten female mice (ddY) having an average body weight of about 20 g in an amount of 0.2 to 0.4 ml, once a day for 7 days. The administration routes and doses are shown below.

| Compound | Route | Dose (mg/kg/day) |
|---|---|---|
| 1 | sc | 1500 |
| | iv | 1500 |
| 2 | sc | 1500 |
| | iv | 1500 |
| A | sc | 1000 |

| Compound | Route | Dose (mg/kg/day) |
|---|---|---|
| | iv | 250 |

During the test period, the body weight of each mouse was measured. On the 7th day, the mice were hematologically examined. After the hematological examination, the mice were killed, and the weights of organs were measured. Also, they were histopathologically observed. Consequently, the following facts were noted.

1. Abnormality was scarcely observed in the group administered with compound 1 and 2 of this invention with regard to body weight gain, hematological examination and histopathological observation. This demonstrates the high safety of the penicillin compounds 1 and 2 of the invention.

2. The group administered with 1000 mg/kg/day (sc) of compound A showed a significant difference from the saline-control group in body weight gain and liver weight. The histopathological observation showed abnormality at the kidneys in this group.

3. Even the group administered with 250 mg/kg/day (iv) of compound A also showed a significant difference from the saline-control group in body weight gain, and the weights of the lungs, liver, kidneys and cecum. The histopathological observation also showed abnormality in the lungs and kidneys.

4. For the reasons given in (2) and (3), compound A is considered to be unacceptable as a medicine.

Example 23 (plasma level)

The contents of the vials (No. A) obtained in Example 17 were dissolved in deionized water to form solutions of compound 1 in a concentration of 100 mg/ml. The solutions were intramuscularly (im) administered to twenty four male mice (ddY) having an average body weight of 26 g at a dose of 25 mg/kg. The plasma level ($\mu$g/ml) of compound 1 was determined, and the results are shown in Table IV.

The other experimental conditions were as follows:
Sampling:

Blood was taken by cardiac puncture from four mice ech 0.25, 0.5, 1, 2, 3 and 4 hours after administration, and centrifuged individually to separate the plasma.

Assay:

Drug levels were determined by the thin-layer cup-plate method using Escherichia coli Kp as an indicator organism. Plasma was appropriately (to more than 10 times) diluted with a 0.067 M phosphate buffer having a pH of 7.0. A standard calibration line was prepared in the same buffer.

Table IV

| Plasma levels of compound 1 in mice (Compound 1 : 25 mg/kg, im, single dose) | | | | | | |
|---|---|---|---|---|---|---|
| | Time after adminitration (hour) | | | | | |
| | 0.25 | 0.5 | 1 | 2 | 3 | 4 |
| Average conc. ($\mu$g/ml) | 27.4 | 21.5 | 15.6 | 9.57 | 4.01 | 2.74 |

It is seen from the results shown in Table IV that the plasma level of the penicillin compound 1 of the invention showed much the same concentration as the MIC ($\mu$g/ml) against various bacteria shown in Table I. Thus, from the viewpoint of plasma level, too, the penicillin compounds of the invention have superior properties as antibacterial agents.

Example 24 (urinary excretion)

The contents of the vials (No. A) obtained in Example 17 were dissolved in deionized water to form solutions of penicillin compound 1 in a concentration of 25 mg/ml. The solutions were administered in a dose of 25 mg/kg (im) to four male mice (ddY) having an average body weight of 25 g. After given periods of time, the urine was collected from the four mice, and the concentration of the penicillin compound 1 in the urine was determined. This experiment was repeated three times, and the averages of the results obtained are shown in Table V.

The other experimental conditions were follows:
Sampling and preparation:

Urine was collected by using a metabolism cage for 3, 6, and 24 hours after administration. The pooled urine was diluted with a 0.067M phosphate buffer (pH 7.0) before assay to 500 times for the 0–3 hour urine, 100 times for the 3–6 hour urine and 10 times for the 6–24 hour urine.

Assay:

The levels of compound 1 were determined by the thin-layer cup-plate method using Escherichia coli Kp as an indicator microorganism and a standard calibration line was prepared in a 0.067M phosphate buffer (pH 7.0).

Table V

| Urinary excretion in mice (Compound 1 : 25 mg/kg, im, single dose) | | | | |
|---|---|---|---|---|
| Body* weight (g) | Item | Time after administration (hour) | | |
| | | 0–3 | 3–6 | 6–24 |
| 101.8 | c | 187 | 21.5 | 7.25 |
| | v | 3.83 | 2.23 | 6.67 |
| | a | 0.718 | 0.0480 | 0.0483 |
| | r | 28.2 | 1.89 | 1.90 |
| | cr | 28.2 | 30.0 | 31.9 |

*total body weight of 4 mice,
c : concentration ($\mu$g/ml),
v : volume (ml),
a : amount (mg),
r : recovery (%),
cr : cumulative recovery (%)

It is seen from Table V that even after 3 to 6 hours after the administration, the urinary level of penicillin compound 1 of the invention is higher than its MIC ($\mu$g/ml) values against various bacteria shown in Table I, and compound 1 of the invention is also very effective against diseases caused by the infection of the urinary tract by various bacteria.

As shown in Tables I to V, the novel penicillin compounds of the invention show a broad range of superior antibacterial activities against various Gram-positive bacteria and Gram-negative bacteria both in an in vitro test and in an in vivo test. In particular, the penicillin compounds of this invention exhibit superior antibacterial activity in parenteral administration against Ampicillin-resistant strains against which Amoxicillin does not exhibit antibacterial activity. They particularly show superior antibacterial activity against bacteria of the genus Pseudomonas against which Amoxicillin and many other known antibiotics are substantially ineffective. Of the various penicillin compounds of this invention, the formyl derivative of formula (Ia), especially its D-isomer, is especially superior in antibacterial activity.

The penicillin compounds of the invention further have great safety as demonstrated by the $LD_{50}$ values given hereinabove, and show chemotherapeutic indices several tens of times as high as those of the known antibiotics such as the known penicillin derivatives having a similar structure to the compound of the invention. The high safety is also supported by the hematological examination and histopathological examination of experimental animals after continual parenteral administration.

The penicillin compounds of the invention further show a high plasma level even several hours after parenteral administration to warm-blooded animals, and maintain a high urinary level over very long periods of time.

The selected novel penicillin compounds of the invention have very superior characteristics to the various known antibacterial agents because of their broad antibacterial spectrum, high antibacterial avitivity, high safety high blood and urinary levels after administration, etc.

It has been found by the present inventors that in using the penicillin compounds of the invention for warm-blooded animals including humans, parenteral administration is far more advantageous than oral administration. In parenteral administration, it is preferred to dissolve the penicillin compound of the invention in a nontoxic liquid medium for injections, and inject the solution intramuscularly, intravenously or subcutaneously.

It is also possible to dissolve, or mix, the penicillin compound of the invention in or with a non-toxic liquid medium or ointment base, and apply the solution or mixture directly to the lesion. It may also be used as a suppository after mixing or dissolving it with or in a suppository base.

Examples of the nontoxic liquid medium used for preparing injections containing the penicillin compound as an active ingredient include sterilized deionized water, a physiological saline solution, a glucose solution, for injection, a Ringer's solution, and an amino acid solution for injection.

The penicillin compound can also be dissolved in other injections, and parenterally administered as such.

The dose of the penicillin compound of the invention in administration to man should be adjusted according to the age, body weight, and condition of the patient, the administering route, the number of administrations, etc. Usually, the dose for adults is 0.1 to 10 g/day, preferably 0.2 to 4 g/day. As stated, in view of their pharmacological properties, the penicillin compounds of this invention are desirably administered parenterally (e.g., intravenously, intramuscularly, or subcutaneously) in the form of an injection dissolved in a pharmaceutically acceptable liquid medium.

The preparations for injection containing the penicillin compounds of this invention are, for example, an injecting set consisting of a vial filled with the penicillin compound as an active ingredient and an ampoule containing an aqueous liquid medium capable of dissolving the active ingredient to form an injection, or an injection prepared by dissolving the active ingredient in an aqueous liquid medium. The aqueous liquid media are those which are usually employed in penicillin or cephalosporin preparations for injection, for example sterilized deionized water containing a known pH adjuster and osmotic pressure adjuster, and if required, a stabilizer. If desired, these preparations may further contain other ingredients according to the purpose of medication.

What we claim is:

1. A member selected from the group consisting of a penicillin compound of the formula

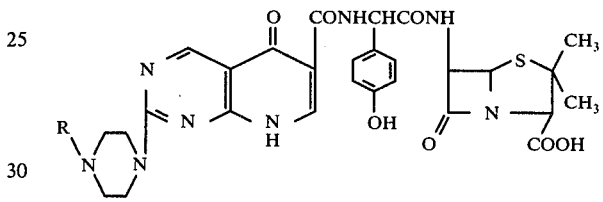

wherein R is a formyl or acetyl group, and a non-toxic pharmaceutically acceptable salt thereof.

2. A member selected from the group consisting of a penicillin compound of the formula

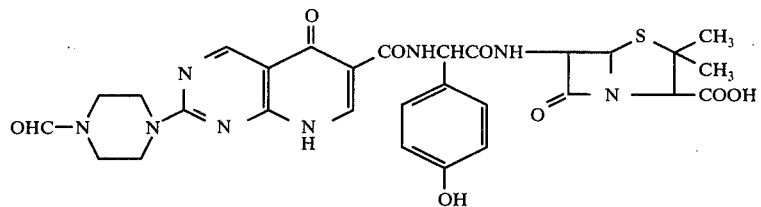

and a non-toxic pharmaceutically acceptable salt thereof.

3. A member selected from the group consisting of D-α-[5,8-dihydro-2-(4-formyl-1-piperazinyl)-5-oxopyrido[2,3-d]pyrimidine-6-carboxamido]-p-hydroxy-benzylpenicillin and a non-toxic pharmaceutically acceptable salt thereof.

4. A member selected from the group consisting of D-α[5,8-dihydro-2-(4-formyl-1-piperazinyl)-5-oxopyrido[2,3-d]pyrimidine-6-carboxamido]-p-hydroxybenzylpenicillin and the sodium or potassium salt thereof.

5. A member selected from the group consisting of a penicillin compound of the formula

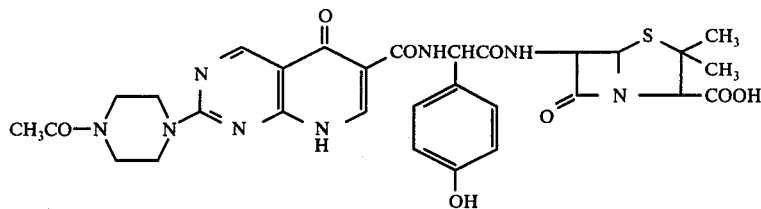

and a non-toxic pharmaceutically acceptable salt thereof.

6. A member selected from the group consisting of D-α-[5,8-dihydro-2-(4-acetyl-1-piperazinyl)-5-oxopyrido[2,3,-d]pyrimidine-6-carboxamido]-p-hydroxybenzylpenicillin and a non-toxic pharmaceutically acceptable salt thereof.

7. A member selected from the group consisting of D-α-[5,8-dihydro-2-(4-acetyl-1-piperazinyl)-5-oxopyrido[2,3-d]pyrimidine-6-carboxamido]-p-hydroxybenzylpenicillin and the sodium or potassium salt thereof.

8. A parenteral, antibacterial solution comprising an antibacterially effective amount of a member selected from the group consisting of a penicillin compound of the formula wherein R is a formyl or acetyl group, and a non-toxic pharmaceutically acceptable salt thereof in a nontoxic liquid medium.

9. A solution according to claim 8 wherein the member is a non-toxic pharmaceutically acceptable salt of D-α-[5,8-dihydro-2-(4-formyl-1-piperazinyl)-5-oxopyrido[2,3-d]pyrimidine-6-carboxamido]-p-hydroxybenzylpenicillin.

10. A solution according to claim 8 wherein the member is a non-toxic pharmaceutically acceptable salt of D-α-[5,8-dihydro-2-(4-acetyl-1-piperazinyl)-5-oxopyrido[2,3-d]pyrimidine-6-carboxamido]-p-hydroxybenzylpenicillin.

11. A method for treating bacterial infections which comprises parenterally administering to a warm-blooded animal an antibacterially effective dose of a compound as defined in claim 1.

12. A method according to claim 11 wherein there is administered a member selected from the group consisting of a compound of the formula

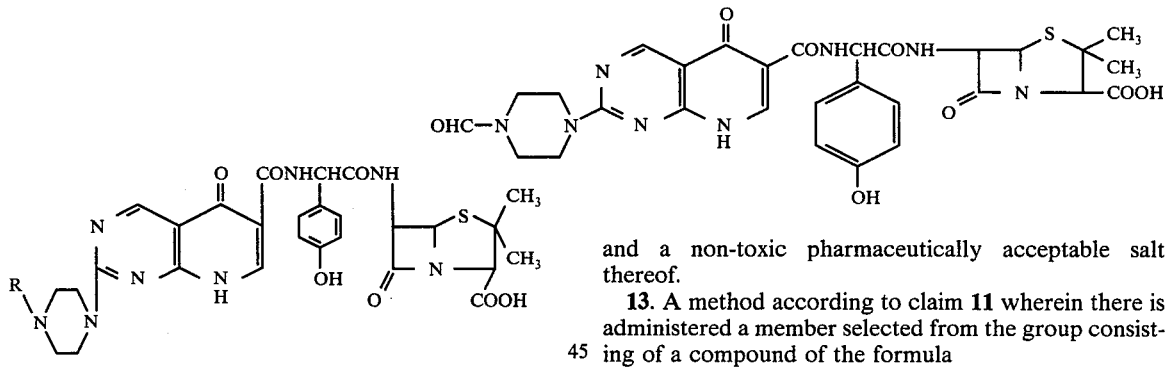

and a non-toxic pharmaceutically acceptable salt thereof.

13. A method according to claim 11 wherein there is administered a member selected from the group consisting of a compound of the formula

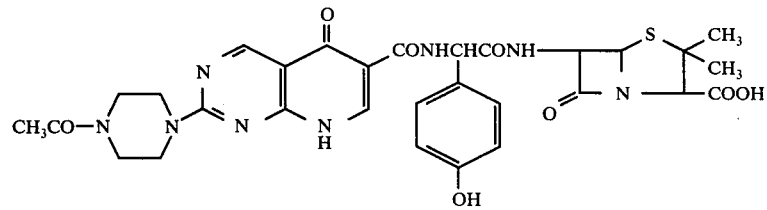

and a non-toxic pharmaceutically acceptable salt thereof.

* * * * *